(12) United States Patent
Andersen et al.

(10) Patent No.: US 7,993,898 B2
(45) Date of Patent: Aug. 9, 2011

(54) CELLULASE VARIANTS

(75) Inventors: Kim Vilbour Andersen, Copenhagen (DK); Martin Schulein, Copenhagen (DK); Torben Henriksen, legal representative, Copenhagen (DK); Lars Christensen, Virum (DK); Bo Damgaard, Lausanne (CH); Claus Von der Osten, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/394,202

(22) Filed: Feb. 27, 2009

(65) Prior Publication Data
US 2009/0170747 A1    Jul. 2, 2009

Related U.S. Application Data

(60) Division of application No. 11/830,063, filed on Jul. 30, 2007, which is a continuation of application No. 10/919,195, filed on Aug. 16, 2004, now abandoned, which is a continuation of application No. 09/261,329, filed on Mar. 3, 1999, now abandoned, which is a continuation of application No. PCT/DK97/00393, filed on Sep. 17, 1997.

(30) Foreign Application Priority Data

Sep. 17, 1996 (DK) ..................... 1013/96

(51) Int. Cl.
*C12N 9/42* (2006.01)
*C12N 1/20* (2006.01)
*C12N 15/00* (2006.01)
*C12Q 1/00* (2006.01)
*C12Q 1/68* (2006.01)
*C12P 21/04* (2006.01)
*C07H 21/04* (2006.01)

(52) U.S. Cl. ............. 435/209; 435/440; 435/252.3; 435/320.1; 435/69.1; 435/71.1; 435/4; 435/6; 536/23.2

(58) Field of Classification Search ............ None
See application file for complete search history.

(56) References Cited

U.S. PATENT DOCUMENTS

| | | |
|---|---|---|
| 5,443,750 A | 8/1995 | Convents et al. |
| 5,520,838 A | 5/1996 | Baeck et al. |
| 5,792,641 A | 8/1998 | Schulein et al. |
| 6,001,639 A | 12/1999 | Schulein et al. |
| 6,114,296 A | 9/2000 | Schulein et al. |

FOREIGN PATENT DOCUMENTS

| | | |
|---|---|---|
| WO | WO 91/10732 | 7/1991 |
| WO | WO 91/17244 | 11/1991 |
| WO | WO 94/07998 | 4/1994 |
| WO | WO 91/17243 | 11/1994 |
| WO | WO 95/02042 | 1/1995 |
| WO | WO 95/24471 | 9/1995 |
| WO | WO 96/17994 | 6/1996 |
| WO | WO 96/23874 | 8/1996 |

OTHER PUBLICATIONS

Branden et al. Introduction to Protein Structure, Garland Publishing Inc., New York, p. 247, 1991.*
Pons et al., Protein Engineering, vol. 8, No. 9, pp. 939-945 (1995).
Hahn et al., Journal of Biological Chemistry, vol. 270, No. 7, pp. 3081-3088 (1995).
Davies et al., Nature, vol. 365, pp. 362-364 (1993).
Henrissat et al., Biochem. Journal, vol. 293, pp. 781-788 (1993).
Schauwecker et al., Blol. Chem. Hoppe-Seyler, vol. 376, pp. 617-625 (1995).
Krengel et al., Journal of Molecular Biology, vol. 263, No. 1, pp. 70-78 (1996).
Park et al., Protein Engineering, vol. 6, No. 8, pp. 921-926 (1993).

* cited by examiner

*Primary Examiner* — Yong D Pak
(74) *Attorney, Agent, or Firm* — Elias Lambiris

(57) ABSTRACT

The present invention relates to a method for improving the properties of a cellulolytic enzyme by amino acid substitution, deletion or insertion, the method comprising the steps of:

a. constructing a multiple alignment of at least two amino acid sequences known to have three-dimensional structures similar to endoglucanase V (EGV) from *Humicola insolens* known from Protein Data Bank entry 4ENG;
b. constructing a homology-built three-dimensional structure of the cellulolytic enzyme based on the structure of the EGV;
c. identifying amino acid residue positions present in a distance from the substrate binding cleft of not more than 5 Å;
d. identifying surface-exposed amino acid residues of the enzyme;
e. identifying all charged or potentially charged amino acid residue positions of the enzyme;
f. choosing one or more positions wherein the amino acid residue is to be substituted, deleted or where an insertion is to be provided; and
g. carrying out the substitution, deletion or insertion by using conventional protein engineering techniques. Also described are cellulase variants obtained by this method.

9 Claims, No Drawings

CELLULASE VARIANTS

CROSS-REFERENCE TO RELATED APPLICATIONS

This application is a division of U.S. application Ser. No. 11/830,063 filed on Jul. 30, 2007, which is a continuation of U.S. application Ser. No. 10/919,195 filed on Aug. 16, 2004, now abandoned, which is a continuation of U.S. application Ser. No. 09/261,329 filed on Mar. 3, 1999, now abandoned, which is a continuation of PCT/DK97/00393 filed on Sep. 17, 1997, which claims priority under 35 U.S.C. 119 of Danish application no. 1013/96 filed on Sep. 17, 1996, the contents of which are fully incorporated herein by reference.

SEQUENCE LISTING

The present application contains information in the form of a sequence listing, which is appended to the application and also submitted on a data carrier accompanying this application. The data carrier is fully incorporated herein by reference.

BACKGROUND OF THE INVENTION

1. Field of the Invention

The present invention relates to cellulase variants, i.e., endo-beta-1,4-glucanase variants, derived from a parental cellulase, i.e., endo-beta-1,4-glucanase, by substitution, insertion and/or deletion, which variant has a catalytic core domain, in which the variant at position 5 holds an alanine residue (A), a serine residue (S), or a threonine residue (T); at position 8 holds a phenylalanine residue (F), or a tyrosine residue (Y); at position 9 holds a phenylalanine residue (F), a tryptophan residue (W), or a tyrosine residue (Y); at position 10 holds an aspartic acid residue (D); and at position 121 holds an aspartic acid residue (D).

2. Description of Related Art

Cellulases or cellulolytic enzymes are enzymes involved in hydrolysis of cellulose. In the hydrolysis of native cellulose, it is known that there are three major types of cellulase enzymes involved, namely cellobiohydrolase (1,4-beta-D-glucan cellobiohydrolase, EC 3.2.1.91), endo-beta-1,4-glucanase (endo-1,4-beta-D-glucan 4-glucanohydrolase, EC 3.2.1.4) and beta-glucosidase (EC 3.2.1.21).

Especially the endo-beta-1,4-glucanases (EC No. 3.2.1.4) constitute an interesting group of hydrolases for the mentioned industrial uses. Endoglucanases catalyses endo hydrolysis of 1,4-beta-D-glycosidic linkages in cellulose, cellulose derivatives (such as carboxy methyl cellulose and hydroxy ethyl cellulose), lichenin, beta-1,4 bonds in mixed beta-1,3 glucans such as cereal beta-D-glucans or xyloglucans and other plant material containing cellulosic parts. The authorized name is endo-1,4-beta-D-glucan 4-glucano hydrolase, but the abbreviated term endoglucanase is used in the present specification. Reference can be made to T.-M. Enveri, "Microbial Cellulases" in W. M. Fogarty, Microbial Enzymes and Biotechnology, Applied Science Publishers, p. 183-224 (1983); Methods in Enzymology, 1988, Vol. 160, pp. 200-391 (edited by Wood, W. A. and Kellogg, S. T.); Béguin, P., "Molecular Biology of Cellulose Degradation", Annu. Rev. Microbiol., 1990, Vol. 44, pp. 219-248; Beguin, P. and Aubert, J.-P., "The biological degradation of cellulose", FEMS Microbiology Reviews, 1994, Vol. 13, pp. 25-58; Henrissat, B., "Cellulases and their interaction with cellulose", Cellulose, 1994, Vol. 1, pp. 169-196.

Cellulases are synthesized by a large number of microorganisms which include fungi, actinomycetes, mycobacteria and true bacteria but also by plants. Especially endoglucanases of a wide variety of specificities have been identified.

A very important industrial use of cellulolytic enzymes is the use for treatment of cellulosic textile or fabric, e.g., as ingredients in detergent compositions or fabric softener compositions, for bio-polishing of new fabric (garment finishing), and for obtaining a "stone-washed" look of cellulose-containing fabric, especially denim, and several methods for such treatment have been suggested, e.g., in GB-A-1 368 599, EP-A-0 307 564 and EP-A-0 435 876, WO 91/17243, WO 91/10732, WO 91/17244, PCT/DK95/000108 and PCT/DK95/00132. Another important industrial use of cellulolytic enzymes is the use for treatment of paper pulp, e.g., for improving the drainage or for deinking of recycled paper.

It is also known that cellulases may or may not have a cellulose binding domain (a CBD). The CBD enhances the binding of the enzyme to a cellulose-containing fiber and increases the efficacy of the catalytic active part of the enzyme Fungi and bacteria produces a spectrum of cellulolytic enzymes (cellulases) which, on the basis of sequence similarities (hydrophobic cluster analysis), can be classified into different families of glycosyl hydrolases [Henrissat B & Bairoch A; Biochem. J., 1993, 293: 781-788]. At present are known cellulases belonging to the families 5, 6, 7, 8, 9, 10, 12, 26, 44, 45, 48, 60, and 61 of glycosyl hydrolases.

Industrially well-performing endo-beta-1,4-glucanases are described in, e.g., WO 91/17243, WO 91/17244 and WO 91/10732, and specific cellulase variants are described in WO 94/07998.

It is an object of the present invention to provide novel variants of cellulolytic enzymes, which variants, when compared to the parental enzyme, show improved performance.

SUMMARY OF THE INVENTION

In a cellulolytic enzyme useful in industrial processes, i.e., an endo-1,4-glucanase, a number of amino acid residue positions important for the properties of the enzyme and thereby for the performance thereof in these processes has been identified.

Accordingly, in a first aspect the present invention provides a method for improving the properties of a cellulolytic enzyme by amino acid substitution, deletion or insertion, the method comprising the steps of:

a. constructing a multiple alignment of at least two amino acid sequences known to have three-dimensional structures similar to endoglucanase V (EGV) from *Humicola insolens* known from Protein Data Bank entry 4ENG;

b. constructing a homology-built three-dimensional structure of the cellulolytic enzyme based on the structure of the EGV;

c. identifying amino acid residue positions present in a distance from the substrate binding cleft of not more than 5 Å;

d. identifying surface-exposed amino acid residues of the enzyme;

e. identifying all charged or potentially charged amino acid residue positions of the enzyme;

f. choosing one or more positions wherein the amino acid residue is to be substituted, deleted or where an insertion is to be provided;

g. carrying out the substitution, deletion or insertion by using conventional protein engineering techniques.

By using the method of the invention, it is now possible effectively to transfer desirable properties from one cellulase to another by protein engineering methods which are known per se.

More particular the invention provides cellulase variants improved with respect to altered (increased or decreased) catalytic activity; and/or altered sensitivity to anionic tensides; and/or altered pH optimum and pH profile activity-wise as well as stability-wise.

Accordingly, in a further aspect, the invention provides a cellulase variant derived from a parental cellulase by substitution, insertion and/or deletion, which variant has a catalytic core domain, in which the variant at position 5 holds an alanine residue (A), a serine residue (S), or a threonine residue (T);

at position 8 holds a phenylalanine residue (F), or a tyrosine residue (Y);

at position 9 holds a phenylalanine residue (F), a tryptophan residue (W), or a tyrosine residue (Y);

at position 10 holds an aspartic acid residue (D); and at position 121 holds an aspartic acid residue (D) (cellulase numbering).

DETAILED DISCLOSURE OF THE INVENTION

Cellulase Variants

The present invention provides new cellulase variants derived from a parental cellulase by substitution, insertion and/or deletion. A cellulase variant of this invention is a cellulase variant or mutated cellulase, having an amino acid sequence not found in nature. The cellulase variants of the invention show improved performance, in particular with respect to increased catalytic activity; and/or altered sensitivity to anionic tensides; and/or altered pH optimum; and/or altered thermostability.

Formally the cellulase variant or mutated cellulase of this invention may be regarded a functional derivative of a parental cellulase (i.e., the native or wild-type enzyme), and may be obtained by alteration of a DNA nucleotide sequence of the parental gene or its derivatives, encoding the parental enzyme. The cellulase variant or mutated cellulase may be expressed and produced when the DNA nucleotide sequence encoding the cellulase variant is inserted into a suitable vector in a suitable host organism. The host organism is not necessarily identical to the organism from which the parental gene originated.

In the literature, enzyme variants have also been referred to as mutants or muteins.

Amino Acids

In the context of this invention the following symbols and abbreviations for amino acids and amino acid residues are used:

| A = | Ala = | Alanine |
| C = | Cys = | Cysteine |
| D = | Asp = | Aspartic acid |
| E = | Glu = | Glutamic acid |
| F = | Phe = | Phenylalanine |
| G = | Gly = | Glycine |
| H = | His = | Histidine |
| I = | Ile = | Isoleucine |
| K = | Lys = | Lysine |
| L = | Leu = | Leucine |
| M = | Met = | Methionine |
| N = | Asn = | Asparagine |
| P = | Pro = | Proline |
| Q = | Gln = | Glutamine |
| R = | Arg = | Arginine |
| S = | Ser = | Serine |
| T = | Thr = | Threonine |
| V = | Val = | Valine |
| W = | Trp = | Tryptophan |
| Y = | Tyr = | Tyrosine |
| B = | Asx = | Asp or Asn |
| Z = | Glx = | Glu or Gln |
| X = | Xaa = | Any amino acid |

\* = Deletion or absent amino acid

Cellulase Numbering

In the context of this invention a specific numbering of amino acid residue positions in cellulolytic enzymes is employed. By aligning the amino acid sequences of known cellulases, as in Table 1 below, it is possible to unambiguously allot an amino acid position number to any amino acid residue in any cellulolytic enzyme, if its amino acid sequence is known.

In Table 1, below, 11 selected amino acid sequences of cellulases of different microbial origin are aligned. These are (a) *Humicola insolens*; (b) *Acremonium* sp.; (c) *Volutella collectotrichoides*; (d) *Sordaria fimicola*; (e) *Thielavia terrestris*; (f) *Fusarium oxysporum*; (g) *Myceliophthora thermophila*; (h) *Crinipellis scabella*; (i) *Macrophomina phaseolina*; (j) *Pseudomonas fluorescens*; (k) *Ustilago maydis*. The cellulases (a-i) are described in WO 96/29397, (j) is described in GeneBank under the accession number G45498, and (k) is described in GeneBank under the accession number S81598 and in Biol. Chem. Hoppe-Seyler, 1995, 376 (10): 617-625.

Using the numbering system originating from the amino acid sequence of the cellulase (endo-beta-1,4-glucanase) obtained from the strain of *Humicola insolens* DSM 1800, disclosed in, e.g., WO 91/17243, which sequence is shown in the first column of Table 1, aligned with the amino acid sequence of a number of other cellulases, it is possible to indicate the position of an amino acid residue in a cellulolytic enzyme unambiguously.

In describing the various cellulase variants produced or contemplated according to the invention, the following nomenclatures are adapted for ease of reference:

[Original amino acid; Position; Substituted amino acid]

Accordingly, the substitution of glutamine with histidine in position 119 is designated as Q119H.

Amino acid residues which represent insertions in relation to the amino acid sequence of the cellulase from *Humicola insolens*, are numbered by the addition of letters in alphabetical order to the preceding cellulase number, such as, e.g., position *21aV for the "inserted" valine (V), where no amino acid residue is present, between lysine at position 21 and alanine at position 22 of the amino acid sequence of the cellulase from *Humicola insolens*, cf. Table 1.

Deletion of a proline (P) at position 49 in the amino acid sequence of the cellulase from *Humicola insolens* is indicated as P49*.

Multiple mutations are separated by slash marks ("/"), e.g., Q119H/Q146R, representing mutations in positions 119 and 146 substituting glutamine (Q) with histidine (H), and glutamine (Q) acid with arginine (R), respectively.

If a substitution is made by mutation in, e.g., a cellulase derived from a strain of *Humicola insolens*, the product is designated, e.g., "*Humicola insolens*/*49P*".

All positions referred to in this application by cellulase numbering refer to the cellulase numbers described above, and are determined relative to the amino acid sequence of the cellulase derived from *Humicola insolens*, cf. Table 1, (a).

TABLE 1

Amino Acid Sequence Alignment:

| | a | b | c | d | e | f | g | h | i | j | k |
|---|---|---|---|---|---|---|---|---|---|---|---|
| 1 | A | G | G | G | G | G | G | T | T | C | * |
| 2 | D | S | T | S | S | S | I | A | S | N | * |
| 3 | G | G | G | G | G | G | G | G | G | G | G |
| 4 | R | H | R | K | Q | H | Q | V | V | Y | M |
| 5 | S | T | T | S | S | S | T | T | T | A | A |
| 6 | T | T | T | T | T | T | T | T | T | T | T |
| 7 | R | R | R | R | R | R | R | R | R | R | R |
| 8 | Y | Y | Y | Y | Y | Y | Y | Y | Y | Y | Y |
| 9 | W | W | W | W | W | W | W | W | W | W | W |
| 10 | D | D | D | D | D | D | D | D | D | D | D |
| 11 | C | C | C | C | C | C | C | C | C | C | C |
| 12 | C | C | C | C | C | C | C | C | C | C | C |
| 13 | K | K | K | K | K | K | K | K | K | L | L |
| 14 | P | P | P | P | P | P | P | P | P | P | A |
| 15 | S | S | S | S | S | S | S | S | S | H | S |
| 16 | C | C | C | C | C | C | C | C | C | A | A |
| 17 | G | A | G | A | A | S | A | G | A | G | S |
| 18 | W | W | W | W | W | W | W | W | W | W | W |
| 19 | A | D | D | S | P | S | P | S | T | S | E |
| 20 | K | E | E | G | G | G | G | G | A | G | |
| 21 | K | K | K | K | K | K | K | K | K | N | K |
| 21a | * | * | * | * | * | * | * | * | * | V | * |
| 22 | A | A | A | A | A | A | G | A | A | P | A |
| 23 | P | A | S | S | S | A | A | P | S | S | P |
| 24 | V | V | V | V | V | V | * | V | V | L | V |
| 25 | N | S | S | N | S | N | S | S | S | V | Y |
| 26 | Q | R | Q | R | Q | A | S | A | K | S | A |
| 27 | P | P | P | P | P | P | P | P | P | P | P |
| 28 | V | V | V | V | V | A | V | V | V | L | V |
| 29 | F | T | K | L | Y | L | Q | R | G | Q | D |
| 30 | S | T | T | A | A | T | A | T | T | S | A |
| 31 | C | C | C | C | C | C | C | C | C | C | C |
| 32 | N | D | D | D | D | D | D | D | D | S | K |
| 33 | A | R | R | A | A | K | K | R | I | A | A |
| 34 | N | N | N | N | N | N | N | N | N | N | D |
| 35 | F | N | N | N | F | D | F | G | D | N | G |
| 36 | Q | S | N | N | Q | N | N | N | N | T | V |
| 37 | R | P | P | P | R | P | P | P | T | A | T |
| 38 | I | L | L | L | L | I | F | L | Q | L | L |
| 39 | T | S | A | N | S | S | N | G | T | S | I |
| 40 | D | P | S | D | D | N | D | P | P | D | D |
| 41 | F | * | * | A | F | T | G | * | S | V | S |
| 42 | D | G | T | N | N | N | G | * | D | S | K |
| 42a | * | * | * | * | * | * | * | S | D | L | * |
| 43 | A | A | A | V | V | A | T | V | L | V | D |
| 44 | K | V | R | K | Q | V | R | K | K | G | P |
| 45 | S | S | S | S | S | S | N | S | S | S | S |
| 46 | G | G | G | G | G | G | G | G | G | S | S |
| 47 | C | C | C | C | C | C | C | C | C | C | C |
| 48 | E | D | D | D | D | N | E | D | D | D | S |
| 49 | P | P | S | * | * | G | A | S | * | * | G |
| 49a | * | * | * | * | * | * | * | * | * | * | C |
| 49b | * | * | * | * | * | * | * | * | * | * | N |
| 50 | G | N | N | G | G | G | G | G | G | G | G |
| 51 | G | G | G | G | G | G | G | G | G | G | G |
| 52 | V | V | V | S | S | S | S | S | T | S | N |
| 53 | A | A | A | A | A | A | A | A | S | A | K |
| 54 | Y | F | Y | Y | Y | Y | Y | Y | F | Y | F |
| 55 | S | T | T | T | S | A | M | T | Y | M | M |
| 56 | C | C | C | C | C | C | C | C | C | C | C |
| 57 | A | N | N | A | A | T | S | A | S | W | S |
| 58 | D | D | D | N | D | N | S | N | N | D | C |
| 59 | Q | N | N | N | Q | Y | Q | N | Q | K | M |
| 60 | T | Q | Q | S | T | S | S | S | G | I | Q |
| 61 | P | P | P | P | P | P | P | P | P | P | P |
| 62 | W | W | W | W | W | W | W | W | F | W | F |
| 63 | A | A | A | A | A | A | A | A | A | A | D |
| 64 | V | V | V | V | V | V | V | V | I | V | D |
| 65 | N | N | N | N | N | N | S | D | N | S | E |
| 66 | D | N | D | D | D | D | D | N | D | P | T |
| 67 | D | N | N | N | N | E | E | N | S | T | D |
| 68 | F | V | L | L | L | L | L | L | T | L | P |
| 69 | A | A | A | A | A | A | S | A | S | A | T |
| 70 | L | Y | Y | Y | Y | Y | Y | Y | Y | Y | L |
| 71 | G | G | G | G | G | G | G | G | G | G | A |
| 72 | F | F | F | F | F | F | W | F | F | Y | F |

TABLE 1-continued

Amino Acid Sequence Alignment:

| | a | b | c | d | e | f | g | h | i | j | k |
|---|---|---|---|---|---|---|---|---|---|---|---|
| 73 | A | A | A | A | A | A | A | A | A | A | G |
| 74 | A | A | A | A | A | A | A | A | A | A | F |
| 75 | T | T | T | T | T | T | V | A | A | T | G |
| 76 | S | A | A | K | S | K | K | H | K | S | A |
| 77 | I | F | F | L | I | I | L | L | L | S | F |
| 78 | A | P | S | S | A | S | A | A | S | G | T |
| 79 | G | G | G | G | G | G | G | G | G | D | T |
| 80 | S | G | G | G | G | G | S | S | K | V | G |
| 81 | N | N | S | T | S | S | S | S | Q | * | Q |
| 82 | E | E | E | E | E | E | E | E | E | * | E |
| 83 | A | A | A | S | S | A | S | A | T | * | S |
| 84 | G | S | S | S | S | S | Q | A | D | * | D |
| 85 | W | W | W | W | W | W | W | W | W | * | T |
| 86 | C | C | C | C | C | C | C | C | C | C | D |
| 87 | C | C | C | C | C | C | C | C | C | G | C |
| 88 | A | A | A | A | A | A | A | Q | G | R | A |
| 89 | C | C | C | C | C | C | C | C | C | C | C |
| 90 | Y | Y | Y | Y | Y | Y | Y | Y | Y | Y | F |
| 91 | E | A | A | A | A | A | E | E | K | Q | Y |
| 92 | L | L | L | L | L | L | L | L | L | L | A |
| 93 | T | Q | Q | T | T | T | T | T | T | Q | E |
| 94 | F | F | F | F | F | F | F | F | F | F | F |
| 95 | T | T | T | T | T | T | T | T | T | T | E |
| 95a | * | * | * | * | * | * | * | * | * | G | * |
| 95b | * | * | * | * | * | * | * | * | * | S | * |
| 95c | * | * | * | * | * | * | * | * | * | S | * |
| 95d | * | * | * | * | * | * | * | * | * | Y | * |
| 95e | * | * | * | * | * | * | * | * | * | N | * |
| 95f | * | * | * | * | * | * | * | * | * | A | * |
| 95g | * | * | * | * | * | * | * | * | * | P | * |
| 95h | * | * | * | * | * | * | * | * | * | G | H |
| 95i | * | * | * | * | * | * | * | * | * | D | D |
| 95j | * | * | * | * | * | * | * | * | * | P | A |
| 95k | * | * | * | * | * | * | * | * | * | G | Q |
| 96 | S | S | S | S | S | T | S | S | S | S | G |
| 97 | G | G | G | G | G | G | G | G | T | A | K |
| 98 | P | P | P | P | P | P | P | P | A | A | A |
| 99 | V | V | V | V | V | V | V | V | V | L | M |
| 100 | A | A | A | S | A | K | A | V | S | A | K |
| 101 | G | G | G | G | G | G | G | G | G | G | R |
| 102 | K | K | K | K | K | K | K | K | K | K | N |
| 103 | K | T | T | T | T | K | K | K | Q | T | K |
| 104 | M | M | M | L | M | M | M | L | M | M | L |
| 105 | V | V | V | V | V | I | I | T | I | I | I |
| 106 | V | V | V | V | V | V | V | V | V | V | F |
| 107 | Q | Q | Q | Q | Q | Q | Q | Q | Q | Q | Q |
| 108 | S | S | S | S | S | S | A | V | I | A | V |
| 109 | T | T | T | T | T | T | T | T | T | T | T |
| 110 | S | N | N | S | S | N | N | N | N | N | N |
| 111 | T | T | T | T | T | T | T | T | T | I | V |
| 112 | G | G | G | G | G | G | G | G | G | G | G |
| 113 | G | G | G | G | G | G | G | G | G | Y | G |
| 114 | D | D | D | D | D | D | D | D | D | D | D |
| 115 | L | L | L | L | L | L | L | L | L | V | V |
| 116 | G | S | S | G | G | G | G | G | G | S | Q |
| 117 | S | G | G | S | S | D | D | N | N | G | S |
| 118 | N | T | N | N | N | N | N | N | N | G | Q |
| 119 | H | H | H | H | Q | H | H | H | H | Q | N |
| 120 | F | F | F | F | F | F | F | F | F | F | F |
| 121 | D | D | D | D | D | D | D | D | D | D | D |
| 122 | L | I | I | L | I | L | L | L | I | I | F |
| 123 | N | Q | L | N | A | M | A | M | A | L | Q |
| 124 | I | M | M | M | M | M | I | I | M | V | I |
| 125 | P | P | P | P | P | P | P | P | P | P | P |
| 126 | G | G | G | G | G | G | G | G | G | G | G |
| 127 | G | G | G | G | G | G | G | G | G | G | G |
| 128 | G | G | G | G | G | G | G | G | G | G | G |
| 129 | V | L | L | V | V | V | V | V | V | V | L |
| 130 | G | G | G | G | G | G | G | G | G | G | G |
| 131 | I | I | I | L | I | I | I | I | L | I | A |
| 132 | F | F | F | F | F | F | F | F | F | F | F |
| 132a | * | * | * | * | * | * | * | * | T | * | P |
| 133 | D | D | D | D | N | D | N | Q | N | N | K |
| 134 | G | G | G | G | G | A | G | G | A | G | G |
| 135 | C | C | C | C | C | C | C | C | C | C | C |
| 136 | T | T | T | K | S | T | T | P | S | S | P |

TABLE 1-continued

Amino Acid Sequence Alignment:

| | a | b | c | d | e | f | g | h | i | j | k |
|---|---|---|---|---|---|---|---|---|---|---|---|
| 137 | P | P | P | R | S | S | D | A | K | A | A |
| 138 | Q | Q | Q | E | Q | E | Q | Q | Q | Q | Q |
| 139 | F | F | W | F | F | F | Y | F | W | W | W |
| 140 | G | G | G | G | G | G | G | G | N | G | G |
| 140a | * | F | V | * | * | K | A | S | G | V | V |
| 141 | G | T | S | G | G | A | P | W | I | S | E |
| 142 | L | F | F | L | L | L | P | N | * | N | A |
| 143 | P | P | P | P | P | G | N | G | * | A | S |
| 143a | * | * | * | * | * | * | G | * | N | E | L |
| 143b | * | * | * | * | * | * | W | * | L | L | W |
| 144 | G | G | G | G | G | G | G | G | G | G | G |
| 145 | Q | N | N | A | A | A | D | A | N | A | D |
| 146 | R | R | R | Q | Q | Q | R | Q | Q | Q | Q |
| 147 | Y | Y | Y | Y | Y | Y | Y | Y | Y | Y | Y |
| 148 | G | G | G | G | G | G | G | G | G | G | G |
| 149 | G | G | G | G | G | G | G | G | G | G | G |
| 150 | I | T | T | I | I | I | I | V | F | F | V |
| 150a | * | * | * | * | * | * | * | * | * | L | * |
| 150b | * | * | * | * | * | * | * | * | * | A | * |
| 150c | * | * | * | * | * | * | * | * | * | A | * |
| 150d | * | * | * | * | * | * | * | * | * | C | * |
| 150e | * | * | * | * | * | * | * | * | * | K | * |
| 150f | * | * | * | * | * | * | * | * | * | Q | * |
| 150g | * | * | * | * | * | * | * | * | * | Q | * |
| 150h | * | * | * | * | * | * | * | * | * | L | * |
| 150i | * | * | * | * | * | * | * | * | * | G | * |
| 150j | * | * | * | * | * | * | * | * | * | y | * |
| 150k | * | * | * | * | * | * | * | * | * | N | * |
| 151 | S | T | T | S | S | S | H | S | T | A | K |
| 152 | S | S | S | S | S | S | S | S | D | S | S |
| 153 | R | R | R | R | R | R | K | R | R | L | A |
| 154 | N | S | S | S | D | S | E | D | S | S | T |
| 155 | E | Q | Q | E | Q | E | E | Q | Q | Q | E |
| 156 | C | C | C | C | C | C | C | C | C | Y | C |
| 157 | D | A | S | D | D | D | E | S | A | K | S |
| 158 | R | E | Q | S | S | S | S | Q | T | S | K |
| 159 | F | L | I | F | F | Y | F | L | L | C | L |
| 160 | P | P | P | P | P | P | P | P | P | V | P |
| 160a | * | * | * | * | * | * | * | * | * | L | * |
| 160b | * | * | * | * | * | * | * | * | * | N | * |
| 160c | * | * | * | * | * | * | * | * | * | R | * |
| 160d | * | * | * | * | * | * | * | * | * | C | * |
| 160e | * | * | * | * | * | * | * | * | * | D | * |
| 160f | * | * | * | * | * | * | * | * | * | S | * |
| 160g | * | * | * | * | * | * | * | * | * | V | * |
| 160h | * | * | * | * | * | * | * | * | * | F | * |
| 160i | * | * | * | * | * | * | * | * | * | G | * |
| 160j | * | * | * | * | * | * | * | * | * | S | * |
| 160k | * | * | * | * | * | * | * | * | * | R | * |
| 160l | * | * | * | * | * | * | * | * | * | G | * |
| 160m | * | * | * | * | * | * | * | * | * | L | * |
| 161 | D | S | S | A | A | E | E | A | S | T | K |
| 162 | A | V | A | A | P | L | A | A | K | Q | P |
| 163 | L | L | L | L | L | L | L | V | W | L | L |
| 164 | K | R | Q | K | K | K | K | Q | Q | Q | Q |
| 165 | P | D | P | P | P | D | P | A | A | Q | E |
| 166 | G | G | G | G | G | G | G | G | S | G | G |
| 167 | C | C | C | C | C | C | C | C | C | C | C |
| 168 | Y | H | N | Q | Q | H | N | Q | N | T | K |
| 169 | W | W | W | W | W | W | W | W | F | W | W |
| 170 | R | R | R | R | R | R | R | R | R | F | R |
| 171 | F | Y | Y | F | F | F | F | F | F | A | F |
| 172 | D | D | D | D | D | D | D | D | D | E | S |
| 173 | W | W | W | W | W | W | W | W | W | E | E |
| 174 | F | F | F | F | F | F | F | M | F | F | W |
| 175 | K | N | N | K | Q | E | Q | G | E | E | G |
| 176 | N | D | D | N | N | N | N | G | N | A | D |
| 177 | A | A | A | A | A | A | A | A | A | A | N |
| 178 | D | D | D | D | D | D | D | D | D | D | P |
| 179 | N | N | N | N | N | N | N | N | N | N | V |
| 180 | P | P | P | P | P | P | P | P | P | P | L |
| 181 | S | N | D | E | T | D | S | N | T | S | K |
| 182 | F | V | V | F | F | F | V | V | V | L | G |
| 183 | S | N | S | T | T | T | T | T | T | D | S |
| 184 | F | W | F | F | F | F | F | F | F | W | P |
| 185 | R | R | R | K | Q | E | Q | R | E | K | K |

TABLE 1-continued

Amino Acid Sequence Alignment:

| | a | b | c | d | e | f | g | h | i | j | k |
|---|---|---|---|---|---|---|---|---|---|---|---|
| 186 | Q | R | R | Q | Q | Q | E | P | P | E | R |
| 187 | V | V | V | V | V | V | V | V | V | V | V |
| 188 | Q | R | Q | Q | Q | Q | A | T | T | P | K |
| 189 | C | C | C | C | C | C | C | C | C | C | C |
| 190 | P | P | P | P | P | P | P | P | P | P | P |
| 191 | A | A | A | S | A | K | S | A | Q | A | K |
| 192 | E | A | A | E | E | A | E | Q | E | E | S |
| 193 | L | L | L | L | I | L | L | L | L | L | L |
| 194 | V | T | T | T | V | L | T | T | V | T | I |
| 195 | A | N | D | S | A | D | S | N | A | T | D |
| 196 | R | R | R | R | R | I | K | I | R | R | R |
| 197 | T | S | T | T | S | S | S | S | T | S | S |
| 198 | G | G | G | G | G | G | G | G | G | G | G |
| 199 | C | C | C | C | C | C | C | C | C | M | C |
| 200 | R | V | R | K | K | K | S | V | S | N | Q |
| 201 | R | R | R | R | R | R | R | R | R | R | R |

Cellulase Numbering of Selected Cellulases of Different Microbial Origin (a) Humicola insolens (SEQ ID NO: 1); (b) Acremonium sp. (SEQ ID NO: 2); (c) Volutella collectotrichoides (SEQ ID NO: 3); (d) Sordaria fimicola (SEQ ID NO: 4); (e) Thielavia terrestris (SEQ ID NO: 5); (f) Fusarium oxysporum (SEQ ID NO: 6); (g) Myceliophthora thermophila (SEQ ID NO: 7); (h) Crinipellis scabella (SEQ ID NO: 8); (i) Macrophomina phaseolina (SEQ ID NO: 9); (j) Pseudomonas fluorescens (SEQ ID NO: 10); (k) Ustilago maydis (SEQ ID NO: 11).
* Amino acid residue absent in this position The Enzyme (Endo-beta-1,4-glucanase) Variants of the Invention The present invention relates to cellulase variants. More specifically the present invention provides cellulase variant derived from a parental cellulase by substitution, insertion and/or deletion, which variant has a catalytic core domain, in which the variant at position 5 holds an alanine residue (A), a serine residue (S), or a threonine residue (T);
at position 8 holds a phenylalanine residue (F) or a tyrosine residue (Y);
at position 9 holds a phenylalanine residue (F), a tryptophan residue (W), or a tyrosine residue (Y);
at position 10 holds an aspartic acid residue (D); and
at position 121 holds an aspartic acid residue (D) (cellulase numbering).

The endoglucanase of the invention may comprise a cellulose binding domain (CBD) existing as an integral part of the enzyme, or a CBD from another origin may be introduced into the endoglucanase thus creating an enzyme hybride. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I-X), and demonstrates that CBDs are found in various enzymes such as cellulases, xylanases, mannanases, arabinofuranosidases, acetyl esterases and chitinases. CBDs have also been found in algae, e.g., the red alga Porphyra purpurea as a non-hydrolytic polysaccharide-binding protein, see Tomme et al., op. cit. However, most of the CBDs are from cellulases and xylanases, CBDs are found at the N and C termini of proteins or are internal. Enzyme hybrids are known in the art, see, e.g., WO 90/00609 and WO 95/16782, and may be prepared by transforming into a host cell a DNA construct comprising at least a fragment of DNA encoding the cellulose-binding domain ligated, with or without a linker, to a DNA sequence encoding the endoglucanase and growing the host cell to express the fused gene.

Enzyme hybrids may be described by the following formula:

CBD-MR-X or X-MR-CBD wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to about 100 amino acids, more preferably of from 2 to 40 amino acids; and X is an N-terminal or C-terminal region of the enzyme according to the invention.

The Method of the Invention

In another aspect, the present invention relates to a method for improving the properties of a cellulolytic enzyme by amino acid substitution, deletion or insertion, the method comprising the steps of:

a. constructing a multiple alignment of at least two amino acid sequences known to have three-dimensional structures similar to endoglucanase V (EGV) from Humicola insolens known from Protein Data Bank entry 4ENG;
b. constructing a homology-built three-dimensional structure of the cellulolytic enzyme based on the structure of the EGV;
c. identifying amino acid residue positions present in a distance from the substrate binding cleft of not more than 5 Å;
d. identifying surface-exposed amino acid residues of the enzyme;
e. identifying all charged or potentially charged amino acid residue positions of the enzyme;
f. choosing one or more positions wherein the amino acid residue is to be substituted, deleted or where an insertion is to be provided;
g. carrying out the substitution, deletion or insertion by using conventional protein engineering techniques.

Step f. of the method is preferably carried out by choosing positions which, as a result of the alignment of step a., carry the same amino acid residue in a majority of the aligned sequences; more preferably in at least 63% of the aligned sequences; even more preferably positions which, in the aligned sequences, carries different amino acid residues, cf. below.

In a preferred embodiment, the specific activity of the cellulase can be improved, preferably by carrying out a substitution, deletion or insertion at amino acid residue positions present in a distance from the substrate binding cleft of not more than 5 Å, more preferably not more than 3 Å, even more preferably not more than 2.5 Å. It is believed that residues present in a distance of not more than 2.5 Å are capable of being in direct contact with the substrate.

In another preferred embodiment, the pH activity profile, the pH activity optimum, the pH stability profile, or the pH stability optimum of the cellulase can be altered, preferably by carrying out a substitution, deletion or insertion at amino acid residue positions present either in a distance from the substrate binding cleft of not more than 5 Å, more preferably not more than 3 Å, even more preferably not more than 2.5 Å; or at surface-exposed amino acid residue positions of the enzyme, thereby altering the electrostatic environment either locally or globally. It is preferred to perform a substitution involving a charged or potentially charged residue, this residue either being the original residue or the replacement residue. In the present context, charged or potentially charged residues are meant to include: Arg, Lys, His, Cys (if not part of a disulfide bridge), Tyr, Glu, and Asp.

In yet another preferred embodiment, the stability of the cellulase in the presence of an anionic tenside or anionic detergent component can be altered, preferably by carrying out a substitution, deletion or insertion at surface-exposed amino acid residue positions of the enzyme, thereby altering the electrostatic environment either locally or globally. It is preferred to perform a substitution involving a charged or potentially charged residue, this residue either being the original residue or the replacement residue. In the present context, charged or potentially charged residues are meant to include: Arg, Lys, His, Cys (if not part of a disulfide bridge), Tyr, Glu, and Asp. Mutations towards a more negatively charged amino acid residue result in improved stability of the cellulase in the presence of an anionic tenside, whereas mutations towards a more positively charged aa residue decreases the stability of the cellulase towards anionic tensides.

Further, cellulase variants comprising any combination of two or more of the amino acid substitutions, deletions or insertions disclosed herein are also within the scope of the present invention, cf. the exemplified variants.

Multiple Sequence Alignment of Cellulases

The multiple sequence alignment is performed using the Pileup algorithm as implemented in the Wisconsin Sequence Analysis Package version 8.1-UNIX (GCG, Genetics Computer Group, Inc.). The method used is similar to the method described by Higgens and Sharp (CARBIOS, 1989, 5, 151-153). A gap creation penalty of 3.0 and a gap extension penalty of 0.1 are used together with a scoring matrix as described in Nucl. Acids Res. 1986, 14 (16), 6745-6763 (Dayhoff table (Schwartz, R. M. and Dayhoff, M. O.; Atlas of Protein Sequence and Structure (Dayhoff, M. O. Ed.); National Biomedical Research Foundation, Washington D.C., 1979, 353-358) rescaled by dividing each value by the sum of its row and column, and normalizing to a mean of 0 and standard deviation of 1.0. The value for FY(Phe-Tyr)=RW=1.425. Perfect matches are set to 1.5 and no matches on any row are better than perfect matches).

Pair-Wise Sequence Alignment of Cellulases

A pair-wise sequence alignment is performed using the algorithm described by Needleman & Wunsch (J. Mol. Biol., 1970, 48, 443-453), as implemented in the GAP routine in the Wisconsin Sequence Analysis Package (GCG). The parameters used for the GAP routine are the same as mentioned for the Pileup routine earlier.

Pair-Wise Sequence Alignment of Cellulases with Forced Pairing

A pair-wise sequence alignment with forced pairing of residues is performed using the algorithm described by Needleman & Wunsch (J. Mol. Biol., 1970, 48, 443-453), as implemented in the GAP routine in the Wisconsin Sequence Analysis Package (GCG). The parameters used for the GAP routine are the same as mentioned for the Pileup routine earlier, where the scoring matrix is modified to incorporate a residue named X which symbolizes the residues to be paired. The diagonal value for X paired with X is set to 9.0 and all off diagonal values involving X is set to 0.

Complex Between *Humicola insolens* Endoglucanase and Celloheptaose

Based on the X-ray structure of the core domain of the *Humicola insolens* EGV endoglucanase inactive variant (D10N) in complex with cellohexaose (Davies et. al.; Biochemistry, 1995, 34, 16210-12220, PDB entry 4ENG) a model of the structure of the native *Humicola insolens* EGV endoglucanase core domain in complex with celloheptaose is build using the following steps:

1. Using the Biopolymer module of the Insight II 95.0 (Insight II 95.0 User Guide, October 1995. San Diego: Biosym/MSI, 1995) replace N10 with a aspartic acid.
2. Make a copy of the sugar unit occupying subsite −3 by copying all the molecule and delete the extra atoms. Manually move the new sugar unit to best fit the unoccupied −1 binding site. Create the bonds to bind the new sugar unit to the two existing cellotriose units.
3. Delete overlapping crystal water molecules. These are identified by using the Subset Interface By_Atom 2.5 command.
4. Build hydrogens at a pH of 8.0 and applying charged terminals
5. Protonate D121 using the Residue Replace <D121 residue name> ASP L command.
6. Apply the CVFF forcefield template through the command Potentials Fix.
7. Fix all atoms except the new sugar unit.
8. Relax the atomic position of the new sugar unit using 300 cycles of simple energy minimization followed by 5000 steps of 1 fs simple molecular dynamics ending by 300 cycles of simple energy minimization all using the molecular mechanics program Discover 95.0/3.0.1 (Discover 95.0/3.0.0 User Guide, October 1995. San Diego: Biosym/MSI, 1995).

Homology Building of Cellulases

The construction of a structural model of a cellulase with known amino acid sequence based on a known X-ray structure of the *Humicola insolens* EGV cellulase consists of the following steps:

1. Define the approximate extend of the core region of the structure to be modeled and the alignment of the cysteine based on multiple sequence alignment between many known industrially useful cellulase sequences.
2. Pair-wise sequence alignment between the new sequence and the sequence of the known X-ray structure.
3. Define Structurally Conserved Regions (SCRs) based on the sequence alignment.
4. Assign coordinates for the model structure within the SCRs.
5. Find structures for the loops or Variable Regions (VRs) between the SCRs by a search in a loop structure database.
6. Assign coordinates for the VRs in the model structure from the database search result.
7. Create disulfide bonds and set protonation state.
8. Refine the build structure using molecular mechanics.

The known X-ray structure of the *Humicola insolens* EGV cellulase will in the following be termed the reference structure. The structure to be modeled will be termed the model structure.

Ad 1: The approximate extent of the core part of the enzyme is determined by a multiple sequence alignment including many known cellulase sequences. Since the reference structure contains only atomic coordinates for the core part of the enzyme only the residues in the sequence to be modeled which align with the core part of the reference structure can be included in the model building. This alignment also determines the alignment of the cysteine. The multiple sequence alignment is performed using the Pileup algorithm as described earlier.

Ad 2: A pair-wise sequence alignment is performed as described earlier. If the cysteine in the conserved disulfide bridges and/or the active site residues (D10 and D121) does not align, a pair-wise sequence alignment using forced pairing of the cysteines in the conserved disulfide bridges and/or the active site residues is performed as described earlier. The main purpose of the sequence alignment is to define SCRs (see later) to be used for a model structure generation.

Ad 3: Based on the sequence alignment Structurally Conserved Regions (SCRs) are defined as continuous regions of overlapping sequence with no insertions or deletions.

Ad 4: Using the computer program Homology 95.0 (Homology User Guide, October 1995. San Diego: Biosym/MSI, 1995.) atomic coordinates in the model structure can be generated from the atomic coordinates of the reference structure using the command AssignCoords Sequences.

Ad 5: Using the computer program Homology 95.0 possible conformations for the remaining regions, named Variable Regions (VRs) are found by a search in the loop structure database included in Homology 95.0. This procedure is performed for each VR.

Ad 6: If the VR length is smaller than six residues the first loop structure in the database search result is selected for coordinate generation. In cases where longer loops are generated the first solution in the list which does not have severe atomic overlap are selected. The degree of atomic overlap can be analyzed using the Bump Monitor Add Intra command in the computer program Insight II 95.0 (Insight II 95.0 User Guide, October 1995. San Diego: Biosym/MSI, 1995.) a parameter of 0.25 for the Bump command will show the severe overlap. If more than ten bumps exists between the inserted loop region and the remaining part of the protein the next solution is tested. If no solution is found with these parameters, the solution with the fewest bumps is selected. The coordinates for the VR regions are generated using the command AssignCoords Loops in the program Homology 95.0.

Ad 7: The disulfide bonds are created using the Bond Create command in the Biopolymer module of Insight II 95.0 and the protonation state is set to match pH 8.0 with charged caps using the Hydrogens command. Finally the active proton donor (the residue equivalent to D121 in the reference structure) is protonated using the residue replace <D121 residue name> ASP L command. To finalize the data of the model the appropriate forcefield template is applied using the CVFF forcefield through the command Potentials Fix.

Ad 8: Finally the modeled structure is subjected to 500 cycles energy minimization using the molecular mechanics program Discover 95.0/3.0.1 (Discover 95.0/3.0.0 User Guide, October 1995. San Diego: Biosym/MSI, 1995.). The output from the above described procedure is atomic coordinates describing a structural model for the core domain of a new cellulase based on sequence homology to the *Humicola insolens* EGV cellulase.

Superpositioning of Cellulase Structures

To overlay two cellulase structures a superposition of the structures are performed using the Structure Alignment command of the Homology 95.0 (Homology User Guide, October 1995. San Diego Biosym/MSI, 1995.). All parameters for the command are chosen as the default values.

Determination of Residues within 3 Å and 5 Å from the Substrate

In order to determine the amino acid residues within a specified distance from the substrate, a given cellulase structure is superimposed on the cellulase part of the model structure of the complex between *Humicola insolens* EGV endoglucanase and celloheptaose as described above. The residues within a specified distance of the substrate are then found using the Interface Subset command of the Insight II 95.0 (Insight II 95.0 User Guide, October 1995, San Diego Biosym/MSI). The specified distance is supplied as parameter to the program.

The results of this determination are presented in Tables 2 and 3 below.

Determination of Surface Accessibility

To determine the solvent accessibility the Access_Surf command in Homology 95.0 (Homology User Guide, October 1995; San Diego: Biosym/MSI, 1995) was used. The program uses the definition proposed by Lee and Richards (Lee, B. & Richards, F. M. "The interpretation of protein structures: Estimation of static accessibility", J. Mol. Biol., 1971, 55, 379-400). A solvent probe radius of 1.4 Å was used and only heavy atoms (i.e., non-hydrogen atoms) were included in the calculation. Residues with zero accessibility are defined as being buried, all other residues are defined as being solvent exposed and on the surface of the enzyme structure.

Transferring Level of Specific Activity Between Cellulases

In order to transfer the level of catalytic activity between two cellulases, the following protocol is applied using the methods described above. This method will pinpoint amino acid residues responsible for the difference in specific activity, and one or more of those amino acid residues must be replaced in one sequence in order to transfer the level of specific activity from the comparison cellulase:

1) Perform multiple sequence alignment of all known industrially useful cellulases (excluding the *Trichoderma reesei* cellulases). From this identify conserved disulfide bridges amongst the two involved sequences and the sequence of the *Humicola insolens* EGV cellulase are identified and the active site residues (D10 and D121) are located;

2) Perform pair-wise sequence alignment of each sequence with the *Humicola insolens* EGV cellulase core domain (residues 1-201). If the cysteines in the conserved disulfide bridges do not align at the same positions and/or if the two active site residues (D10 and D121) do not align at the same positions then use the pair-wise sequence alignment of cellulases with forced pairing method. Include only residues in the sequences overlapping with the core domain (residues 1-201) of the *Humicola insolens* EGV cellulase;

3) Create a homology build structure of each sequence;

4) Determination of residues within 3 Å from the substrate in each of the homology build structures. Differences between the sequences in these positions will most probably be the residues responsible for the difference in specific activity. In the case where residues in inserts are found in any of the sequences within the above mentioned distance, the complete insert can be responsible for the difference in specific activity, and the complete insert must be transferred to the sequence without the insert or the complete insert must be deleted in the sequence with the insert;

5) If not all specific activity was restored by substitution of residues within 3 Å of the substrate, determination of residues within 5 Å from the substrate in each of the homology build structures will reveal the most probable residues responsible for the remaining difference in specific activity. In the case where residues in inserts are found in any of the sequences within the above mentioned distance, the complete insert can be responsible for the difference in specific activity, and the complete insert must be transferred to the sequence without the insert or the complete insert must be deleted in the sequence with the insert.

Transferring the Level of Stability Towards Anionic Tensides Between Cellulases

In order to transfer level of stability towards anionic tensides between two cellulases, the following protocol is applied using the methods described above. This method will pinpoint amino acid residues responsible for the difference in level of stability towards anionic tensides, and one or more of those amino acid residues must be replaced in one sequence in order to transfer the level of specific activity from the comparison cellulase:

1) Perform multiple sequence alignment of all known industrially useful cellulases (excluding *Trichoderma reesei* cellulases). From this identify conserved disulfide bridges amongst the two involved sequences and the sequence of the *Humicola insolens* EGV cellulase are identified and the active site residues (D10 and D121) are located;
2) Perform pair-wise sequence alignment of each sequence with the *Humicola insolens* EGV cellulase core domain (residues 1-201). If the cysteines in the conserved disulfide bridges do not align at the same positions and/or if the two active site residues (D10 and D121) do not align at the same positions then use the pair-wise sequence alignment of cellulases with forced pairing method. Include only residues in the sequences overlapping with the core domain (residues 1-201) of the *Humicola insolens* EGV cellulase;
3) Create a homology build structure of each sequence;
4) Determination of residues located at the surface of the enzyme. This is done by calculation the surface accessibility. Residues with a surface accessibility greater than 0.0 Å$^2$ are exposed to the surface;
5) Any residue exposed to the surface belonging to the following group of amino acids: D, E, H, K, R and C if not involved in a disulfide bridge which differs between the two sequences will most probably be responsible for the difference in level of stability towards anionic tensides. In the case where residues in inserts are found in any of the sequences within the above mentioned group of amino acid types, the complete insert can be responsible for the difference in level of stability towards anionic tensides, and the complete insert must be transferred to the sequence without the insert or the complete insert must be deleted in the sequence with the insert.

Disulfide Bridges

Disulfide bridges (i.e., Cys-Cys bridges) stabilize the structure of the enzyme. It is believed that a certain number of stabilizing disulfide bridges is necessary to maintain a proper stability of the enzyme. However, it is also contemplated that disulfide bridges can be removed from the protein structure resulting in an enzyme variant which is less stable, especially less thermostable, but which still has significant activity.

Therefore, in another aspect, the invention provides a cellulase variant which variant holds 4 or more of the following disulfide bridges: C11-C135; C12-C47; C16-C86; C31-C56; C87-C199; C89-C189; and C156-C167 (cellulase numbering). In a more specific embodiment the variant of the invention holds 5 or more of the following disulfide bridges: C11-C135; C12-C47; C16-C86; C31-C56; C87-C199; C89-C189; and C156-C167 (cellulase numbering). In its most specific embodiment, the variant of the invention holds 6 or more of the following disulfide bridges: C11-C135; C12-C47; C16-C86; C31-C56; C87-C199; C89-C189; and C156-C167 (cellulase numbering).

In another embodiment the invention provides a cellulase variant in which cysteine has been replaced by another natural amino acid at one or more of the positions 16, 86, 87, 89, 189, and/or 199 (cellulase numbering).

Binding Cleft Substitutions

In a further aspect, the invention provides a cellulase variant derived from a parental cellulase by substitution, insertion and/or deletion at one or more amino acid residues located in the substrate binding cleft. Mutations introduced at positions close to the substrate affect the enzyme-substrate interactive bindings.

An appropriate way of determining the residues interacting with a potential substrate in a structure is to partitionate the structure in "shells". The shells are defined as: 1st shell are residues directly interacting with the substrate, i.e., closest inter atomic distance between substrate and residue both including hydrogen atoms are smaller than 2.5 Å which will include all direct interaction via hydrogen bonds and other non bonded interactions. The subsequent (2nd, 3rd e.t.c.) shells are defined in the same way, as the residues with inter atomic distances smaller than 2.5 Å to the substrate or all previously determined shells. In this way the structure will be partitioned in shells. The routine "subset zone" in the program Insight II 95.0 (Insight II 95.0 User Guide, October 1995. San Diego: Biosym/MSI, 1995.) can be used to determine the shells.

In a preferred embodiment, the amino acid residue contemplated according to this invention is located in the substrate binding cleft at a distance of up to 5 Å from the substrate.

When subjecting the aligned cellulases to the computer modeling method disclosed above, the following positions within a distance of up to 5 Å from the substrate are revealed: 4, 5, 6, 7, 8, 9, 10, 11, 12, 13, 14, 15, 16, 18, 19, 20, 21, 21a, 42, 44, 45, 47, 48, 49, 49a, 49b, 74, 82, 95j, 110, 111, 112, 113, 114, 115, 116, 119, 121, 123, 127, 128, 129, 130, 131, 132, 132a, 133, 145, 146, 147, 148, 149, 150b, 178, and/or 179 (cellulase numbering), cf. Table 2.

Accordingly, in a more specific embodiment, the invention provides a cellulase variant which has been derived from a parental cellulase by substitution, insertion and/or deletion at one or more of these acid residues. In a particular embodiment, the cellulase variant is derived from one of the cellulases identified in Table 2 ((a) *Humicola insolens*; (b) *Acremonium* sp.; (c) *Volutella collectotrichoides*; (d) *Sordaria fimicola*; (e) *Thielavia terrestris*; (f) *Fusarium oxysporum*; (g) *Myceliophthora thermophila*; (h) *Crinipellis scabella*; (i) *Macrophomina phaseolina*; a) *Pseudomonas fluorescens*; (k) *Ustilago maydis*), by substitution, insertion and/or deletion at one or more of the positions identified in Table 2 for these cellulases.

TABLE 2

Amino Acid Residues less than 5 Å from the Substrate

| | a | b | c | d | e | f | g | h | i | j | k |
|---|---|---|---|---|---|---|---|---|---|---|---|
| 4 | | | | | | | | | | Y | |
| 5 | S | T | T | S | S | S | T | T | T | A | A |
| 6 | T | T | T | T | T | T | T | T | T | T | T |
| 7 | R | R | R | R | R | R | R | R | R | R | R |
| 8 | Y | Y | Y | Y | Y | Y | Y | Y | Y | Y | Y |
| 9 | W | W | W | W | W | W | W | W | W | W | W |

TABLE 2-continued

Amino Acid Residues less than 5 Å from the Substrate

| | a | b | c | d | e | f | g | h | i | j | k |
|---|---|---|---|---|---|---|---|---|---|---|---|
| 10 | D | D | D | D | D | D | D | D | D | D | D |
| 11 | | | | | | | C | | | | |
| 12 | C | C | C | C | C | C | C | C | C | C | C |
| 13 | K | K | K | K | K | K | K | K | K | K | L |
| 14 | P | P | P | P | P | P | P | P | P | P | A |
| 15 | S | S | S | S | S | S | S | S | S | H | S |
| 16 | | | | | | | C | | | | |
| 18 | W | W | W | W | W | W | W | W | W | W | W |
| 19 | A | D | D | S | P | S | P | S | T | | E |
| 20 | K | E | E | | G | | G | G | | A | |
| 21 | K | K | K | K | K | K | K | K | K | | K |
| 21a | | | | | | | | | | V | |
| 42 | | G | T | | | | | | | D | |
| 44 | | V | R | K | Q | V | R | | | | G |
| 45 | S | S | S | S | S | N | S | S | S | S | |
| 47 | C | C | C | C | C | C | C | C | C | C | |
| 48 | E | D | D | D | N | E | D | D | D | D | S |
| 49 | | P | | | | | | | | | |
| 49a | | | | | | | | | | | C |
| 49b | | | | | | | | | | | N |
| 74 | A | A | A | A | A | A | A | A | A | A | F |
| 82 | E | E | E | E | E | E | | E | E | | E |
| 95j | | | | | | | | | | P | |
| 110 | S | N | N | S | S | N | N | N | N | N | N |
| 111 | T | T | T | T | T | T | T | T | T | I | V |
| 112 | G | G | G | G | G | G | G | G | G | G | G |
| 113 | G | G | G | G | G | G | G | G | G | Y | G |
| 114 | D | D | D | D | D | D | D | D | D | D | D |
| 115 | L | L | L | L | L | L | L | L | L | V | V |
| 116 | | | | | | | G | | | | |
| 119 | H | H | H | H | Q | H | H | H | H | Q | N |
| 121 | D | D | D | D | D | D | D | D | D | D | D |
| 123 | | Q | | | | | | | | | |
| 127 | G | G | G | G | G | G | G | G | G | G | G |
| 128 | G | G | G | G | G | G | G | G | G | G | G |
| 129 | V | L | L | V | V | V | V | V | V | V | L |
| 130 | G | G | G | G | G | G | G | G | G | G | G |
| 131 | I | I | I | L | I | I | I | L | I | A | A |

TABLE 2-continued

Amino Acid Residues less than 5 Å from the Substrate

| | a | b | c | d | e | f | g | h | i | j | k |
|---|---|---|---|---|---|---|---|---|---|---|---|
| 132 | F | F | F | F | F | F | F | F | F | F | F |
| 132a | | | | | | | | T | | | P |
| 133 | | | | | | | | | N | N | |
| 145 | | | | | | | | | | A | D |
| 146 | R | R | R | Q | Q | Q | R | Q | Q | Q | Q |
| 147 | Y | Y | Y | Y | Y | Y | Y | Y | Y | Y | Y |
| 148 | G | G | G | G | G | G | G | G | G | G | G |
| 149 | G | | G | G | G | | | G | | | |
| 150b | | | | | | | | | | A | |
| 178 | D | D | D | D | D | D | D | D | D | D | P |
| 179 | N | N | N | N | N | N | N | N | N | N | V |

Positions Identified by Cellulase Numbering (a) *Humicola insolens*; (b) *Acremonium sp.*; (c) *Volutella collectotrichoides*; (d) *Sordaria fimicola*; (e) *Thielavia terrestris*; (f) *Fusarium oxysporum*; (g) *Myceliophthora thermophila*; (h) *Crinipellis scabella*; (i) *Macrophomina phaseolina*; (j) *Pseudomonas fluorescens*; (k) *Ustilago maydis*.

In another preferred embodiment, the amino acid residue contemplated according to this invention is located in the substrate binding cleft at a distance of up to 3 Å from the substrate.

When subjecting the aligned cellulases to the computer modeling method disclosed above, the following positions within a distance of up to 3 Å from the substrate are revealed: 6, 7, 8, 10, 12, 13, 14, 15, 18, 20, 21, 45, 48, 74, 110, 111, 112, 113, 114, 115, 119, 121, 127, 128, 129, 130, 131, 132, 132a, 146, 147, 148, 150b, 178, and/or 179 (cellulase numbering). cf. Table 3.

Accordingly, in a more specific embodiment, the invention provides a cellulase variant which has been derived from a parental cellulase by substitution, insertion and/or deletion at one or more of these acid residues. In a particular embodiment, the cellulase variant is derived from one of the cellulases identified in Table 3 ((a) *Humicola insolens*; (b) *Acremonium sp.*; (c) *Volutella collectotrichoides*; (d) *Sordaria fimicola*; (e) *Thielavia terrestris*; (f) *Fusarium oxysporum*; (g) *Myceliophthora thermophila*; (h) *Crinipellis scabella*; (i) *Macrophomina phaseolina*; (j) *Pseudomonas fluorescens*; (k) *Ustilago maydis*), by substitution, insertion and/or deletion at one or more of the positions identified in Table 3 for these cellulases.

TABLE 3

Amino Acid Residues less than 3 Å from the Substrate

| | a | b | c | D | e | f | g | h | i | j | K |
|---|---|---|---|---|---|---|---|---|---|---|---|
| 6 | T | T | T | T | T | T | T | T | T | T | T |
| 7 | R | R | R | R | R | R | R | R | R | R | R |
| 8 | Y | Y | Y | Y | Y | Y | Y | Y | Y | Y | Y |
| 10 | D | D | D | D | D | D | D | | D | D | |

TABLE 3-continued

Amino Acid Residues less than 3 Å from the Substrate

| | a | b | c | D | e | f | g | h | i | j | K |
|---|---|---|---|---|---|---|---|---|---|---|---|
| 12 | C | C | C | C | C | C | C | C | C | C | C |
| 13 | K | K | K | K | | K | | | K | | L |
| 14 | | P | | | P | P | P | P | P | | A |
| 15 | S | S | S | S | S | S | S | S | S | H | S |
| 18 | W | W | W | W | W | W | W | W | W | W | W |
| 20 | | E | E | | | | | | | | |
| 21 | K | | | K | | | | | | | |
| 45 | S | S | S | S | S | N | S | S | S | S | S |
| 48 | | D | | | N | E | D | | | D | |
| 74 | A | | | A | A | A | A | A | A | | F |
| 110 | | N | N | | S | N | N | N | N | N | N |
| 111 | T | T | T | T | T | T | T | T | T | | |
| 112 | G | G | G | G | G | G | G | G | G | G | G |
| 113 | G | G | G | G | | | | G | G | Y | G |
| 114 | D | D | D | D | D | D | D | D | D | D | D |
| 115 | L | L | L | L | L | L | L | L | L | V | V |
| 119 | H | H | H | | Q | H | | H | | Q | |
| 121 | D | D | D | D | D | D | D | D | D | D | D |
| 127 | G | | | G | G | G | G | | G | | |
| 128 | G | | | G | G | G | G | G | G | | G |
| 129 | V | L | L | V | V | V | V | V | V | V | L |
| 130 | G | G | G | G | G | G | G | G | G | G | G |
| 131 | I | I | I | L | I | I | I | L | I | A | A |
| 132 | F | F | F | F | F | F | F | F | F | F | F |
| 132a | | | | | | | | T | | | P |
| 146 | | | | | Q | | | Q | | Q | Q |
| 147 | Y | Y | Y | Y | Y | Y | Y | Y | Y | Y | Y |
| 148 | G | G | G | G | G | G | G | G | G | G | G |
| 150b | | | | | | | | | | | A |
| 178 | D | D | D | D | | | | D | | D | P |
| 179 | N | N | N | N | N | N | N | N | N | N | V |

Positions Identified by Cellulase Numbering (a) *Humicola insolens*; (b) *Acremonium sp.*; (c) *Volutella collectotrichoides*; (d) *Sordaria fimicola*; (e) *Thielavia terrestris*; (f) *Fusarium oxysporum*; (g) *Myceliophthora thermophila*; (h) *Crinipellis scabella*; (i) *Macrophomina phaseolina*; (j) *Pseudomonas fluorescens*; (k) *Ustilago maydis*.

Partly Conserved Amino Acid Residues

As defined herein a "partly conserved amino acid residue" is an amino acid residue identified according to Table 1, at a position at which position between 7 to 10 amino acid residues of the 11 residues (i.e., more than 63%) indicated in Table 1 for that position, are identical.

Accordingly, the invention further provides a cellulase variant, in which variant an amino acid residue has been changed into a conserved amino acid residue at one or more positions according to Table 1, at which position(s) between 7 and 10 amino acid residues of the 11 residues identified in Table 1, are identical.

In a preferred embodiment the invention provides a cellulase variant, which has been derived from a parental cellulase by substitution, insertion and/or deletion at one or more of the following positions: 13, 14, 15, 20, 21, 22, 24, 28, 32, 34, 45, 48, 50, 53, 54, 62, 63, 64, 65, 66, 68, 69, 70, 71, 72, 73, 74, 75, 79, 85, 88, 90, 92, 93, 95, 96, 97, 98, 99, 104, 106, 110, 111, 113, 115, 116, 118, 119, 131, 134, 138, 140, 146, 152, 153, 163, 166, 169, 170, 171, 172, 173, 174, 174, 177, 178, 179, 180, 193, 196, and/or 197 (cellulase numbering).

In a more specific embodiment the invention provides a cellulase variant that has been subjected to substitutions, insertions and/or deletions, so as to comprise one or more of the amino acid residues at the positions identified in Table 4, below. The positions in Table 4 reflects the "partly conserved amino acid residue positions" as well as the non-conserved positions present within 5 Å of the substrate in binding cleft all of which indeed are present in the aligned sequences in Table 1.

TABLE 4

Selected Substitutions, Insertions and/or Deletions
Positions Identified by Cellulase Numbering

| Position | Amino Acid Residue |
|---|---|
| 4 | R, H, K, Q, V, Y, M |
| 5 | S, T, A |
| 13 | K, L |
| 14 | P, A |
| 15 | H, S |
| 16 | C, A |
| 19 | A, D, S, P, T, E |
| 20 | A, E, G, K |
| 21 | K, N |
| 21a | V, * |
| 22 | A, G, P |
| 24 | *, L, V |
| 28 | A, L, V |
| 32 | D, K, N, S |
| 34 | D, N |
| 38 | F, I, L, Q |
| 42 | D, G, T, N, S, K, * |
| 44 | K, V, R, Q, G, P |
| 45 | N, S |
| 46 | G, S |
| 47 | C, Q |
| 48 | D, E, N, S |
| 49 | P, S, A, G, * |
| 49a | C, * |
| 49b | N, * |
| 50 | G, N |
| 53 | A, G, K, S |
| 54 | F, Y |
| 62 | F, W |
| 63 | A, D |
| 64 | D, I V |
| 65 | D, E, N, S |
| 66 | D, N, P, T |
| 68 | F, L, P, T, V |
| 69 | A, S, T |
| 70 | L, Y |
| 71 | A, G |
| 72 | F, W, Y |
| 73 | A, G |
| 74 | A, F |
| 75 | A, G, T, V |
| 79 | G, T |
| 82 | E, * |
| 88 | A, G, Q, R |

TABLE 4-continued

Selected Substitutions, Insertions and/or Deletions
Positions Identified by Cellulase Numbering

| Position | Amino Acid Residue |
|---|---|
| 90 | F, Y |
| 92 | A, L |
| 93 | E, Q, T |
| 95 | E, T |
| 95j | P, * |
| 96 | S, T |
| 97 | A, G, T |
| 98 | A, P |
| 99 | L, V |
| 104 | L, M |
| 106 | F, V |
| 110 | N, S |
| 111 | I, T, V |
| 113 | G, Y |
| 115 | L, V |
| 116 | G, Q, S |
| 118 | G, N, Q, T |
| 119 | H, N, Q |
| 129 | L, V |
| 131 | A, I, L |
| 132 | A, P, T, * |
| 133 | D, K, N, Q |
| 134 | A, G |
| 138 | E, Q |
| 145 | A, D, N, Q |
| 146 | Q, R |
| 150b | A, * |
| 152 | D, S |
| 153 | A, K, L, R |
| 163 | L, V, W |
| 166 | G, S |
| 169 | F, W |
| 170 | F, R |
| 171 | A, F, Y |
| 172 | D, E, S |
| 173 | E, W |
| 174 | F, M, W |

TABLE 4-continued

Selected Substitutions, Insertions and/or Deletions
Positions Identified by Cellulase Numbering

| Position | Amino Acid Residue |
|---|---|
| 177 | A, N |
| 178 | D, P |
| 179 | N, V |
| 180 | L, P |
| 193 | I, L |
| 196 | I, K, R |
| 197 | S, T |

In a yet more preferred embodiment, the invention provides a cellulase variant derived from a parental cellulase by substitution, insertion and/or deletion at one or more amino acid residues as indicated in Tables 5-6, below. The cellulase variant may be derived from any parental cellulase holding the amino acid residue stated at the position indicated. In particular the parental cellulase may be a *Humicola insolens* cellulase; an *Acremonium* sp. Cellulase; a *Volutella collectotrichoides* cellulase; a *Sordaria fimicola* cellulase; a *Thielavia terrestris* cellulase; a *Fusarium oxysporum* cellulase; a *Myceliophthora thermophila* cellulase; a *Crinipellis scabella* cellulase; a *Macrophomina phaseolina* cellulase; a *Pseudomonas fluorescens* cellulase; or a *Ustilago maydis* cellulase.

Moreover, the cellulase variant may be characterized by having improved performance, in particular with respect to 1. improved performance defined as increased catalytic activity;
2. altered sensitivity to anionic tenside; and/or
3. altered pH optimum;

as also indicated in Tables 5-6. The positions listed in Table 5 reflect transfer of properties between the different cellulases aligned in Table 1. The positions listed in Table 6 reflect transfer of properties from *Humicola insolens* EGV to the other cellulases aligned in Table 1.

TABLE 5

Preferred Cellulase Variants
Positions Identified by Cellulase Numbering

K13L, L13K (1, 2, 3);
P14A, A14P (1);
S15H, H15S (1, 3);
K20E, K20G, K20A, E20K, G20K, A20K, E20G, E20A, G20E, A20E, G20A, A20G (1, 2, 3);
K21N, N21K (1, 2, 3);
A22G, A22P, G22A, P22A, G22P, P22G (1);
V24*, V24L, *24V, L24V, *24L, L24* (1);
V28A, V28L, A28V, L28V, A28L, L28A (1);
N32D, N32S, N32K, D32N, S32N, K32N, D32S, D32K, S32D, S32K, K32D, S32K, K32S (2, 3);
N34D, D34N (2);
I38L, I38F, I38Q, L38I, F38I, Q38I, L38F, L38Q, F38L, Q38L, F38Q, Q38F (1)
S45N, N45S (1);
G46S, S46G (1);
E48D, E48N, D48E, N48E, D48N, N48D (1, 2, 3);
G50N, N50G (1);
A53S, A53G, A53K, S53A, G53A, K53A, S53G, S53K, G53S, S53K, G53K, K53G (1);
Y54F, F54Y (1, 3);
W62F, F62W (1, 2);
A63D, D63A (2, 3);
V64I, V64D, I64V, D64V, I64D, D64I (2);
N65S, N65D, N65E, S65N, D65N, E65N, S65D, S65E, D65S, E65S, D65E, E65D (2);
D66N, D66P, D66T, N66D, P66D, T66D, N66P, N66T, P66N, T66N, P66T, T66P (2, 3);
F68V, F68L, F68T, F68P, V68F, L68F, T68F, P68F, V68L, V68T, V68P, L68V, T68V, P68V, L68T, L68P, T68L, P68L, T68P, P68T (1, 2);
A69S, A69T, S69A, T69A, S69T, T69S (1);
L70Y, Y70L (1);
G71A, A71G (1);
F72W, F72Y, W72F, Y72F, W72Y, Y72W (1);
A73G, G73A (1);
A74F, F74A (1);

TABLE 5-continued

Preferred Cellulase Variants
Positions Identified by Cellulase Numbering T75V, T75A, T75G, V75T, A75T, G75T, V75A, V75G, A75V, G75V, A75G, G75A (1);
G79T, T79G (1);
W85T, T85W (1);
A88Q, A88G, A88R, Q88A, G88A, R88A, Q88G, Q88R, G88Q, R88Q, G88R, R88G (1, 2, 3);
Y90F, F90Y (1);
L92A, A92L (1);
T93Q, T93E, Q93T, E93T, Q93E, E93Q (2);
T95E, E95T (2);
S96T, T96S (1);
G97T, G97A, T97G, A97G, T97A, A97T (1);
P98A, A98P (1);
V99L, L99V (1);
M104L, L104M (1);
V106F, F106V (1, 3);
S110N, N110S (1);
T111I, T111V, I111T, V111T, I111V, V111I (1);
G113Y, Y113G (1, 3);
L115V, V115L (1);
G116S, G116Q, S116G, Q116G, S116Q, Q116S (1);
N118T, N118G, N118Q, T118N, G118N, Q118N, T118G, T118Q, G118T, Q118T, G118Q, Q118G (1);
H119Q, H119N, Q119H, N119H (1, 2);
V129L, L129V (1);
I131L, I131A, L131I, A131I, L131A, A131L (1);
G134A, A134G (1);
Q138E, E138Q (1, 2, 3);
G140N, N140G (1);
R146Q, Q146R (1, 2, 3);
S152D, D152S (2);
R153K, R153L, R153A, K153R, L153R, A153R, K153L, K153A, L153K, A153K, L153A, A153L (2);
L163V, L163W, V163L, W163L, V163W, W163V (1);
G166S, S166G (1);
W169F, F169W (1);
R170F, F170R (1, 2, 3);
F171Y, F171A, Y171F, A171F, Y171A, A171Y (1);
D172E, D172S, E172D, S172D, E172S, S172E (2);
W173E, E173W (1, 2, 3);
F174M, F174W, M174F, W174F, M174W, W174M (1);
A177N, N177A (1);
D178P, P178D (1, 2, 3);
N179V, V179N (1);
P180L, L180P (1);
L193I, I193L (1);
R196I, R196K, I196R, K196R, I196K, K196I (2, 3);
T197S, S197T (1)

TABLE 6

Preferred Cellulase Variants
Positions Identified by Cellulase Numbering L13K (1, 2, 3);
A14P (1);
H15S (1, 3);
E20K, G20K, A20K (1, 2, 3);
N21K (1, 2, 3);
G22A, P22A (1);
*24V, L24V (1);
A28V, L28V (1);
D32N, S32N, K32N (2, 3);
D34N (2);
L38I, F38I, Q38I (1);
N45S (1);
S46G (1);
D48E, N48E (1, 2, 3);
N50G (1);
S53A, G53A, K53A (1);
F54Y (1, 3);
F62W (1, 2);
D63A (2, 3);
I64V, D64V (2);
S65N, D65N, E65N (2)
N66D, P66D, T66D (2, 3);
V68F, L68F, T68F, P68F (1, 2);
S69A, T69A (1)
Y70L (1)
A71G (1)
W72F, Y72F (1)
G73A (1)
F74A (1)
V75T, A75T, G75T (1)
T79G (1);
T85W (1);
Q88A, G88A, R88A (1, 2, 3)
F90Y (1)
A92L (1)
Q93T, E93T (2);
E95T (2);
T96S (1);
T97G, A97G (1);
A98P (1);
L99V (1);
L104M (1);
F106V (1, 3);
N110S (1);

TABLE 6-continued

Preferred Cellulase Variants
Positions Identified by Cellulase Numbering

I111T, V111T (1);
Y113G (1, 3);
V115L (1);
S116G, Q116G (1);
T118N, G118N, Q118N (1);
Q119H, N119H (1, 2);
L129V (1);
L131I, A131I (1);
A134G (1);
E138Q (1, 2, 3);
N140G (1);
Q146R (1, 2, 3);
D152S (2);
K153R, L153R, A153R (2);
V163L, W163L (1);
S166G (1);
F169W (1);
F170R (1, 2, 3);
Y171F, A171F (1);
E172D, S172D (2);
E173W (1, 2, 3);
M174F, W174F (1);
N177A (1);
P178D (1, 2, 3);
V179N (1);
L180P (1);
I193L (1);
I196R, K196R (2, 3);
S197T (1)

Altered Sensibility Towards Anionic Tensides

As mentioned above, anionic tensides are products frequently incorporated into detergent compositions. Sometimes cellulolytic enzymes having an increased stability towards anionic tensides are desired, and sometimes cellulolytic enzymes having an increased sensitivity are preferred. In a further aspect the invention provides cellulase variants having an altered anionic tenside sensitivity.

Accordingly, a cellulase variant of the invention of altered anionic tenside sensitivity is a cellulase variant which has been derived from a parental cellulase by substitution, insertion and/or deletion at one or more of the following positions: 2, 4, 7, 8, 10, 13, 15, 19, 20, 21, 25, 26, 29, 32, 33, 34, 35, 37, 40, 42, 42a, 43, 44, 48, 53, 54, 55, 58, 59, 63, 64, 65, 66, 67, 70, 72, 76, 79, 80, 82, 84, 86, 88, 90, 91, 93, 95, 95d, 95h, 95j, 97, 100, 101, 102, 103, 113, 114, 117, 119, 121, 133, 136, 137, 138, 139, 140a, 141, 143a, 145, 146, 147, 150e, 150j, 151, 152, 153, 154, 155, 156, 157, 158, 159, 160c, 160e, 160k, 161, 162, 164, 165, 168, 170, 171, 172, 173, 175, 176, 178, 181, 183, 184, 185, 186, 188, 191, 192, 195, 196, 200, and/or 201 (cellulase numbering). These positions contain, in at least one of the cellulase sequences aligned in Table 1, a charged or potentially charged aa residue.

In a particular embodiment, the cellulase variant is derived from one of the cellulases identified in Table 7, below, ((a) *Humicola insolens*; (b) *Acremonium* sp.; (c) *Volutella collectotrichoides*; (d) *Sordaria fimicola*; (e) *Thielavia terrestris*; (f) *Fusarium oxysporum*; (g) *Myceliophthora thermophila*; (h) *Crinipellis scabella*; (i) *Macrophomina phaseolina*; (j) *Pseudomonas fluorescens*; (k) *Ustilago maydis*), by substitution, insertion and/or deletion at one or more of the positions identified in Table 7 for these cellulases.

TABLE 7

Altered Sensitivity towards Anionic Tensides

| | a | b | c | d | e | f | g | h | i | j | k |
|---|---|---|---|---|---|---|---|---|---|---|---|
| 2 | D | | | | | | | | | | |
| 4 | R | H | R | K | | H | | | Y | | |
| 7 | R | R | R | R | R | R | R | R | R | R | R |
| 8 | Y | Y | Y | Y | Y | Y | Y | Y | Y | Y | Y |
| 10 | D | D | D | D | D | D | D | D | D | D | D |
| 13 | K | K | K | K | K | K | K | K | K | | |
| 15 | | | | | | | | | H | | |
| 19 | | D | D | | | | | | | | E |
| 20 | K | E | E | | | | | | | | |
| 21 | K | K | K | K | K | K | K | K | K | | K |
| 25 | | | | | | | | | | | Y |
| 26 | | R | | R | | | | | K | | |
| 29 | | | K | | Y | | | R | | | D |
| 32 | | D | D | D | D | D | D | D | D | | K |
| 33 | | R | R | | | K | K | R | | | |
| 34 | | | | | | | | | | | D |
| 35 | | | | | | D | D | | D | | |
| 37 | R | | | | R | | | | R | | |
| 40 | D | | D | D | | D | | | D | D | |
| 42 | D | | | | | | | | D | | K |
| 42a | | | | | | | | | D | | K |
| 43 | | | | | | | | | | | D |
| 44 | K | | R | K | | | R | K | K | | |
| 48 | E | D | D | D | | E | D | D | D | | |
| 53 | | | | | | | | | | | K |
| 54 | Y | | Y | Y | Y | Y | | Y | Y | | |
| 55 | | | | | | | | | Y | | |
| 58 | D | D | D | | D | | | | D | | |
| 59 | | | | | | Y | | | K | | |
| 63 | | | | | | | | | | | D |
| 64 | | | | | | | | | | | D |
| 65 | | | | | | | | D | | | E |
| 66 | D | | D | D | D | D | | D | | | |
| 67 | D | | | | E | E | | | | | D |
| 70 | | Y | Y | Y | Y | Y | Y | Y | Y | | |
| 72 | | | | | | | | | Y | | |
| 76 | | | K | | K | K | H | K | | | |
| 79 | | | | | | | | | D | | |

TABLE 7-continued

Altered Sensitivity towards Anionic Tensides

| | a | b | c | d | e | f | g | h | i | j | k |
|---|---|---|---|---|---|---|---|---|---|---|---|
| 80 | | | | | | | | | | K | |
| 82 | E | E | E | E | E | E | E | E | E | | E |
| 84 | | | | | | | | | D | | D |
| 86 | | | | | | | | | | | D |
| 88 | | | | | | | | | | R | |
| 90 | Y | Y | Y | Y | Y | Y | Y | Y | Y | Y | |
| 91 | E | | | | | | E | E | K | | Y |
| 93 | | | | | | | | | | | E |
| 95 | | | | | | | | | | | E |
| 95d | | | | | | | | | Y | | |
| 95h | | | | | | | | | | | H |
| 95i | | | | | | | | | D | | D |
| 97 | | | | | | | | | | | K |
| 100 | | | | | | K | | | | | K |
| 101 | | | | | | | | | | | R |
| 102 | K | K | K | K | K | K | K | K | K | K | |
| 103 | K | | | | K | K | K | | | | K |
| 113 | | | | | | | | | | Y | |
| 114 | D | D | D | D | D | D | D | D | D | D | D |
| 117 | | | | | D | D | | | | | |
| 119 | H | H | H | H | | H | H | H | H | | |
| 121 | D | D | D | D | D | D | D | D | D | | |
| 133 | D | D | D | D | D | | | | | | K |
| 136 | | | | K | | | | | | | |
| 137 | | | R | | D | | K | | | | |
| 138 | | | | E | E | | | | | | |
| 139 | | | | | | | | | Y | | |
| 140a | | | | | K | | | | | | |
| 141 | | | | | | | | | | | E |
| 143a | | | | | | | | | E | L | |
| 145 | | | | | | | | D | | | D |
| 146 | R | R | R | | | | | R | | | |
| 147 | Y | Y | Y | Y | Y | Y | Y | Y | Y | Y | Y |
| 150e | | | | | | | | | | | K |
| 150j | | | | | | | | | | Y | |
| 151 | | | | | | | | H | | | K |
| 152 | | | | | | | | | | D | |
| 153 | R | R | R | R | R | R | K | R | R | | |
| 154 | | | | D | | E | D | | | | |
| 155 | E | | | E | | E | | E | | | E |
| 156 | | | | | | | | | | Y | |
| 157 | D | | | D | D | D | E | | | | K |
| 158 | R | E | | | | | | | | | K |
| 159 | | | | | | | | Y | | | |
| 160c | | | | | | | | | | | R |
| 160e | | | | | | | | | | D | |
| 160k | | | | | | | | | | | R |
| 161 | D | | | | | E | E | | | | K |
| 162 | | | | | | | | | K | | |
| 164 | K | R | | K | K | K | K | | | | |
| 165 | | D | | | D | | | | | | E |
| 168 | Y | H | | | H | | | | | | K |
| 170 | R | R | R | R | R | R | R | R | | | R |
| 171 | | Y | Y | | | | | | | | |
| 172 | D | D | D | D | D | D | D | D | D | E | |
| 173 | | | | | | | | | | | E |
| 175 | K | | | K | E | | | | E | E | |
| 176 | | D | D | | | | | | | | D |
| 178 | D | D | D | D | D | D | D | D | D | D | |
| 181 | | D | E | D | | | | | | | K |
| 183 | | | | | | | | | D | K | |
| 184 | | | | | | | | | | Y | |
| 185 | R | R | R | K | E | | | R | E | K | K |
| 186 | | R | R | | | E | | | | E | R |
| 188 | | R | | | | | | | | | K |
| 191 | | | | | | | K | | | | K |
| 192 | E | | | E | E | E | | E | E | | |
| 195 | | | D | | D | | | | | | D |
| 196 | R | R | R | R | R | | K | | R | R | |
| 200 | R | | R | K | K | K | | | | | |
| 201 | R | R | R | R | R | R | R | R | R | | R |

Positions Identified by Cellulase Numbering (a) *Humicola insolens*; (b) *Acremonium sp.*; (c) *Volutella collectotrichoides*; (d) *Sordaria fimicola*; (e) *Thielavia terrestris*; (f) *Fusarium oxysporum*; (g) *Myceliophthora thermophila*; (h) *Crinipellis scabella*; (i) *Macrophomina phaseolina*; (j) *Pseudomonas fluorescens*; (k) *Ustilago maydis*.

Enzyme Compositions

In a still further aspect, the present invention relates to an enzyme composition comprising an enzyme exhibiting cellulolytic activity as described above.

The enzyme composition of the invention may, in addition to the cellulase of the invention, comprise one or more other enzyme types, for instance hemi-cellulase such as xylanase and mannanase, other cellulase components, chitinase, lipase, esterase, pectinase, cutinase, phytase, oxidoreductase, peroxidase, laccase, oxidase, pactinmethylesterase, polygalacturonase, protease, or amylase.

The enzyme composition may be prepared in accordance with methods known in the art and may be in the form of a liquid or a dry composition. For instance, the enzyme composition may be in the form of a granulate or a microgranulate. The enzyme to be included in the composition may be stabilized in accordance with methods known in the art.

Examples are given below of preferred uses of the enzyme composition of the invention. The dosage of the enzyme composition of the invention and other conditions under which the composition is used may be determined on the basis of methods known in the art.

The enzyme composition according to the invention may be useful for at least one of the following purposes.

Uses

During washing and wearing, dyestuff from dyed fabrics or garment will conventionally bleed from the fabric which then looks faded and worn. Removal of surface fibers from the fabric will partly restore the original colors and looks of the fabric. By the term "color clarification", as used herein, is meant the partly restoration of the initial colors of fabric or garment throughout multiple washing cycles.

The term "de-pilling" denotes removing of pills from the fabric surface.

The term "soaking liquor" denotes an aqueous liquor in which laundry may be immersed prior to being subjected to a conventional washing process. The soaking liquor may contain one or more ingredients conventionally used in a washing or laundering process.

The term "washing liquor" denotes an aqueous liquor in which laundry is subjected to a washing process, i.e., usually a combined chemical and mechanical action either manually or in a washing machine. Conventionally, the washing liquor is an aqueous solution of a powder or liquid detergent composition.

The term "rinsing liquor" denotes an aqueous liquor in which laundry is immersed and treated, conventionally immediately after being subjected to a washing process, in order to rinse the laundry, i.e., essentially remove the detergent solution from the laundry. The rinsing liquor may contain a fabric conditioning or softening composition.

The laundry subjected to the method of the present invention may be conventional washable laundry. Preferably, the major part of the laundry is sewn or un-sewn fabrics, including knits, wovens, denims, yarns, and toweling, made from cotton, cotton blends or natural or manmade cellulosics (e.g., originating from xylan-containing cellulose fibers such as from wood pulp) or blends thereof. Examples of blends are blends of cotton or rayon/viscose with one or more companion material such as wool, synthetic fibers (e.g., polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g., rayon/viscose, ramie, flax/linen, jute, cellulose acetate fibers, lyocell).

DETERGENT DISCLOSURE AND EXAMPLES

Surfactant System

The detergent compositions according to the present invention comprise a surfactant system, wherein the surfactant can be selected from nonionic and/or anionic and/or cationic and/or ampholytic and/or zwitterionic and/or semi-polar surfactants.

The surfactant is typically present at a level from 0.1% to 60% by weight.

The surfactant is preferably formulated to be compatible with enzyme components present in the composition. In liquid or gel compositions the surfactant is most preferably formulated in such a way that it promotes, or at least does not degrade, the stability of any enzyme in these compositions.

Preferred systems to be used according to the present invention comprise as a surfactant one or more of the nonionic and/or anionic surfactants described herein.

Polyethylene, polypropylene, and polybutylene oxide condensates of alkyl phenols are suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (The condensation product of C11-C15 linear alcohol with 9 moles ethylene oxide), Tergitol™ 24-L-6 NMW (the condensation product of C12-C14 primary alcohol with 6 moles ethylene oxide with a narrow molecular weight distribution), both marketed by Union Carbide Corporation; Neodol™ 45-9 (the condensation product of C14-C15 linear alcohol with 9 moles of ethylene oxide), Neodol™ 23-3 (the condensation product of C12-C13 linear alcohol with 3 moles of ethylene oxide), Neodol™ 45-7 (the condensation product of C14-C15 linear alcohol with 7 moles of ethylene oxide), Neodol™ 45-5 (the condensation product of C14-C15 linear alcohol with 5 moles of ethylene oxide) marketed by Shell Chemical Company, Kyro™ EOB (the condensation product of C13-C15 alcohol with 9 moles ethylene oxide), marketed by The Procter & Gamble Company, and Genapol LA 050 (the condensation product of C12-C14 alcohol with 5 moles of ethylene oxide) marketed by Hoechst. Preferred range of HLB in these products is from 8-11 and most preferred from 8-10.

Also useful as the nonionic surfactant of the surfactant systems of the present invention are alkylpolysaccharides disclosed in U.S. Pat. No. 4,565,647, having a hydrophobic group containing from about 6 to about 30 carbon atoms, preferably from about 10 to about 16 carbon atoms and a polysaccharide, e.g., a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkylpolyglycosides have the formula

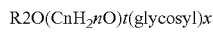

wherein R2 is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethyleneoxide, alkylpolysaccharides, and mixtures hereof. Most preferred are C8-C14 alkyl phenol ethoxylates having from 3 to 15 ethoxy groups and C8-C18 alcohol ethoxylates (preferably C10 avg.) having from 2 to 10 ethoxy groups, and mixtures thereof.

Highly preferred nonionic surfactants are polyhydroxy fatty acid amide surfactants of the formula

wherein R1 is H, or R1 is C1-4 hydrocarbyl, 2-hydroxyethyl, 2-hydroxypropyl or a mixture thereof, R2 is C5-31 hydrocarbyl, and Z is a polyhydroxyhydrocarbyl having a linear hydrocarbyl chain with at least 3 hydroxyls directly connected to the chain, or an alkoxylated derivative thereof. Preferably, R1 is methyl, R2 is straight C11-15 alkyl or C16-18 alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulfate surfactants. Examples hereof are water soluble salts or acids of the formula RO(A)mSO3M wherein R is an unsubstituted C10-C24 alkyl or hydroxyalkyl group having a C10-C24 alkyl component, preferably a C12-C20 alkyl or hydro-xyalkyl, more preferably C12-C18 alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperidinium cations and those derived from alkylamines such as ethylamine, diethylamine, triethylamine, mixtures thereof, and the like. Exemplary surfactants are C12-C18 alkyl polyethoxylate (1.0) sulfate (C12-C18E(1.0) M), C12-C18 alkyl polyethoxylate (2.25) sulfate (C12-C18 (2.25)M, and C12-C18 alkyl polyethoxylate (3.0) sulfate (C12-C18E(3.0)M), and C12-C18 alkyl polyethoxylate (4.0) sulfate (C12-C18E(4.0)M), wherein M is conveniently selected from sodium and potassium.

Suitable anionic surfactants to be used are alkyl ester sulfonate surfactants including linear esters of C8-C20 carboxylic acids (i.e., fatty acids) which are sulfonated with gaseous SO₃ according to "The Journal of the American Oil Chemists Society", 52, 1975, pp. 323-329. Suitable starting materials would include natural fatty substances as derived from tallow, palm oil, etc.

The preferred alkyl ester sulfonate surfactant, especially for laundry applications, comprises alkyl ester sulfonate surfactant of the structural formula:

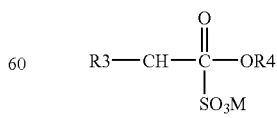

wherein R3 is a C8-C20 hydrocarbyl, preferably an alkyl, or combination thereof, R4 is a C1-C6 hydrocarbyl, preferably an alkyl, or combination thereof, and M is a cation which forms a water soluble salt with the alkyl ester sulfonate.

Suitable salt-forming cations include metals such as sodium, potassium, and lithium, and substituted or unsubstituted ammonium cations, such as monoethanolamine, diethanolamine, and triethanolamine. Preferably, R3 is C10-C16 alkyl, and R4 is methyl, ethyl or isopropyl. Especially preferred are the methyl ester sulfonates wherein R3 is C10-C16 alkyl.

Other suitable anionic surfactants include the alkyl sulfate surfactants which are water soluble salts or acids of the formula $ROSO_3M$ wherein R preferably is a C10-C24 hydrocarbyl, preferably an alkyl or hydroxyalkyl having a C10-C20 alkyl component, more preferably a C12-C18 alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations such as tetramethyl-ammonium and dimethyl piperidinium cations and quaternary ammonium cations derived from alkylamines such as ethylamine, diethylamine, triethylamine, and mixtures thereof, and the like). Typically, alkyl chains of C12-C16 are preferred for lower wash temperatures (e.g., below about 50° C.) and C16-C18 alkyl chains are preferred for higher wash temperatures (e.g., above about 50° C.).

Other anionic surfactants useful for detersive purposes can also be included in the laundry detergent compositions of the present invention. Theses can include salts (including, for example, sodium, potassium, ammonium, and substituted ammonium salts such as mono-di- and triethanolamine salts) of soap, C8-C22 primary or secondary alkanesulfonates, C8-C24 olefinsulfonates, sulfonated polycarboxylic acids prepared by sulfonation of the pyrolyzed product of alkaline earth metal citrates, e.g., as described in British patent specification No. 1,082,179, C8-C24 alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated C12-C18 monoesters) and diesters of sulfosuccinates (especially saturated and unsaturated C6-C12 diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)k$-$CH_2COO$-$M+$ wherein R is a C8-C22 alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vols. I and II by Schwartz, Perry and Berch). A variety of such surfactants are also generally disclosed in U.S. Pat. No. 3,929,678 (column 23, line 58 through column 29, line 23, herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

wherein R2 is an alkyl or alkyl benzyl group having from about 8 to about 18 carbon atoms in the alkyl chain, each R3 is selected form the group consisting of —$CH_2CH_2$—, —$CH_2CH(CH_3)$—, —$CH_2CH(CH_2OH)$—, —$CH_2CH_2CH_2$—, and mixtures thereof; each R4 is selected from the group consisting of C1-C4 alkyl, C1-C4 hydroxyalkyl, benzyl ring structures formed by joining the two R4 groups, —$CH_2CHOHCHOHCOR6CHOHCH_2OH$, wherein R6 is any hexose or hexose polymer having a molecular weight less than about 1000, and hydrogen when y is not 0; R5 is the same as R4 or is an alkyl chain, wherein the total number of carbon atoms or R2 plus R5 is not more than about 18; each y is from 0 to about 10, and the sum of the y values is from 0 to about 15; and X is any compatible anion.

Highly preferred cationic surfactants are the water soluble quaternary ammonium compounds useful in the present composition having the formula:

 (i)

wherein R1 is C8-C16 alkyl, each of R2, R3 and R4 is independently C1-C4 alkyl, C1-C4 hydroxy alkyl, benzyl, and —$(C_2H_4O)xH$ where x has a value from 2 to 5, and X is an anion. Not more than one of R2, R3 or R4 should be benzyl.

The preferred alkyl chain length for R1 is C12-C15, particularly where the alkyl group is a mixture of chain lengths derived from coconut or palm kernel fat or is derived synthetically by olefin build up or OXO alcohols synthesis.

Preferred groups for R2, R3 and R4 are methyl and hydroxyethyl groups and the anion X may be selected from halide, methosulphate, acetate and phosphate ions.

Examples of suitable quaternary ammonium compounds of formulae (i) for use herein are:
coconut trimethyl ammonium chloride or bromide;
coconut methyl dihydroxyethyl ammonium chloride or bromide;
decyl triethyl ammonium chloride;
decyl dimethyl hydroxyethyl ammonium chloride or bromide;
C12-15 dimethyl hydroxyethyl ammonium chloride or bromide;
coconut dimethyl hydroxyethyl ammonium chloride or bromide;
myristyl trimethyl ammonium methyl sulphate;
lauryl dimethyl benzyl ammonium chloride or bromide;
lauryl dimethyl(ethenoxy)4 ammonium chloride or bromide;
choline esters (compounds of formula (i) wherein R1 is

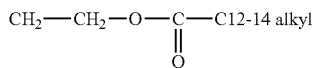

and R2R3R4 are methyl).
di-alkyl imidazolines [compounds of formula (i)].
Other cationic surfactants useful herein are also described in U.S. Pat. No. 4,228,044 and in EP 000 224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight or branched-chain. One of the aliphatic substituents contains at least about 8 carbon atoms, typically from about 8 to about 18 carbon atoms, and at least one contains an anionic water-solubilizing group, e.g., carboxy, sulfonate, sulfate. See U.S. Pat. No. 3,929,678 (column 19, lines 18-35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

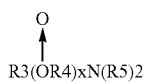

wherein R3 is an alkyl, hydroxyalkyl, or alkyl phenyl group or mixtures thereof containing from about 8 to about 22 carbon atoms; R4 is an alkylene or hydroxyalkylene group containing from about 2 to about 3 carbon atoms or mixtures thereof; x is from 0 to about 3: and each R5 is an alkyl or hydroxyalkyl group containing from about 1 to about 3 carbon atoms or a polyethylene oxide group containing from about 1 to about 3 ethylene oxide groups. The R5 groups can be attached to each other, e.g., through an oxygen or nitrogen atom, to form a ring structure.

These amine oxide surfactants in particular include C10-C18 alkyl dimethyl amine oxides and C8-C12 alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Builder System

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g., SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy)diacetic acid, maleic acid, diglycolic acid, tartaric acid, tartronic acid and fumaric acid, as well as the ether carboxylates described in German Offenle-enschrift 2,446,686, and 2,446,487, U.S. Pat. No. 3,935,257 and the sulfinyl carboxylates described in Belgian Patent No. 840, 623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2,-ethane tetracarboxylates, 1,1,3,3-propane tetracarboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadienide pentacarboxylates, 2,3,4,5-tetrahydro-furan-cis,cis,cis-tetracarboxylates, 2,5-tetrahydro-furan-cis, discarboxylates, 2,2, 5,5,-tetrahydrofuran-tetracarboxylates, 1,2,3,4,5,6-hexane-hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxy-carboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N, N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include Na$_2$EDDS and Na$_4$EDDS. Examples of such preferred magnesium salts of EDDS include MgEDDS and Mg$_2$EDDS. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000-5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Preferred detergent compositions, in addition to the enzyme preparation of the invention, comprise other enzyme(s) which provides cleaning performance and/or fabric care benefits.

Such enzymes include proteases, lipases, cutinases, amylases, cellulases, peroxidases, oxidases (e.g., laccases).

Proteases: Any protease suitable for use in alkaline solutions can be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270.

Preferred commercially available protease enzymes include those sold under the trade names Alcalase, Savinase, Primase, Durazym, and Esperase by Novo Nordisk A/S (Denmark), those sold under the tradename Maxatase, Maxacal, Maxapem, Properase, Purafect and Purafect OXP by Genencor International, and those sold under the tradename Opticlean and Optimase by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Lipases: Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a *Candida* lipase, such as a *C. antarctica* lipase, e.g., the *C. antarctica* lipase A or B described in EP 214 761, a *Pseudomonas* lipase such as a *P. alcaligenes* and *P. pseudoalcaligenes* lipase, e.g., as described in EP 218 272, a *P. cepacia* lipase, e.g., as described in EP 331 376, a *P. stutzeri* lipase, e.g., as disclosed in GB 1,372,034, a *P. fluorescens* lipase, a *Bacillus* lipase, e.g., a *B. subtilis* lipase (Dartois et al., 1993, Biochemica et Biophysica acta 1131, 253-260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., 1991, Gene 103, 61-67), the *Geotricum candidum* lipase (Schimada, Y. et al., 1989, J. Biochem., 106, 383-388), and various *Rhizopus* lipases such as a *R. delemar* lipase (Hass, M. J. et al., 1991, Gene 109, 117-113), a *R. niveus* lipase (Kugimiya et al., 1992, Biosci. Biotech. Biochem. 56, 716-719) and an *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g., described in WO 90/09446).

Especially suitable lipases are lipases such as M1 Lipase™, Luma Fast™ and Lipomax™ (Genencor), Lipolase™ and Lipolase Ultra™ (Novo Nordisk A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases: Any amylase (alpha and/or beta) suitable for use in alkaline solutions can be used. Suitable amylases include those of bacterial or fungal origin. Chemically or genetically modified mutants are included. Amylases include, for example, a-amylases obtained from a special strain of *B. licheniformis*, described in more detail in GB 1,296,839. Commercially available amylases are Duramyl™, Termamyl™, Fungamyl™ and BAN™ (available from Novo Nordisk A/S) and Rapidase™ and Maxamyl P™ (available from Genencor).

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Cellulases: Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307, which discloses fungal cellulases produced from *Humicola insolens*. Especially suitable cellulases are the cellulases having color care benefits. Examples of such cellulases are cellulases described in European patent application No. 0 495 257 and the endoglucanase of the present invention.

Commercially available cellulases include Celluzyme™ produced by a strain of *Humicola insolens* (Novo Nordisk A/S), and KAC-500(B)™ (Kao Corporation).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Peroxidases/Oxidases: Peroxidase enzymes are used in combination with hydrogen peroxide or a source thereof (e.g., a percarbonate, perborate or persulfate). Oxidase enzymes are used in combination with oxygen. Both types of enzymes are used for "solution bleaching", i.e., to prevent transfer of a textile dye from a dyed fabric to another fabric when said fabrics are washed together in a wash liquor, preferably together with an enhancing agent as described in, e.g., WO 94/12621 and WO 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Mixtures of the above mentioned enzymes are encompassed herein, in particular a mixture of a protease, an amylase, a lipase and/or a cellulase.

The enzyme of the invention, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Bleaching Agents

Additional optional detergent ingredients that can be included in the detergent compositions of the present invention include bleaching agents such as PB1, PB4 and percarbonate with a particle size of 400-800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g., granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, EP 0 133 354 and U.S. Pat. No. 4,412,934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5-10% by weight of the finished product, preferably 1-5% by weight.

The hydrogen peroxide releasing agents can be used in combination with bleach activators such as tetra-acetylethylenediamine (TAED), nonanoyloxybenzenesulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8 (6-octanamido-caproyl)oxybenzenesulfonate, C9 (6-nonanamido caproyl)oxybenzenesulfonate and C10 (6-decanamido caproyl)oxybenzenesulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. Ser. No. 08/136,626.

The hydrogen peroxide may also be present by adding an enzymatic system (i.e., an enzyme and a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a manganese catalyst. The manganese catalyst may, e.g., be one of the compounds described in "Efficient manganese catalysts for low-temperature bleaching", Nature, 1994, Vol. 369, pp. 637-639.

Suds Suppressors

Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or water-dispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Application EP 0 593 841.

Especially preferred silicone suds controlling agents are described in European Patent Application No. 92201649.8. Said compositions can comprise a silicone/silica mixture in combination with fumed nonporous silica such as Aerosil®.

The suds suppressors described above are normally employed at levels of from 0.001% to 2% by weight of the composition, preferably from 0.01% to 1% by weight.

Other Components

Other components used in detergent compositions may be employed such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2' disulphonate, disodium 4,4'-bis-(2-morpholino-4-anilino-s-triazin-6-ylamino-stilbene-2:2'-disulphonate, disodium 4,4'-bis-(2,4-dianilino-s-triazin-6-ylamino)stilbene-2:2'-disulphonate, monosodium 4',4"-bis-(2,4-dianilino-s-tri-azin-6 ylamino) stilbene-2-sulphonate, disodium 4,4'-bis-(2-anilino-4-(N-methyl-N-2-hydroxyethylamino)-s-triazin-6-ylamino)stilbene-2,2'-disulphonate, disodium 4,4'-bis-(4-phenyl-2,1,3-triazol-2-yl)-stilbene-2,2'-disulphonate, disodium 4,4'-bis(2-anilino-4-(1-methyl-2-hydroxyethylamino)-s-triazin-6-ylamino)stilbene-2,2'-disulphonate, sodium 2(stilbyl-4"-(naphtho-1',2':4,5)-1,2,3-triazole-2"-sulphonate and 4,4'-bis (2-sulphostyryl)biphenyl.

Other useful polymeric materials are the polyethylene glycols, particularly those of molecular weight 1000-10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. Nos. 4,116,885 and 4,711,730 and EP 0 272 033. A particular preferred polymer in accordance with EP 0 272 033 has the formula:

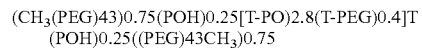

where PEG is —(OC$_2$H$_4$)0-, PO is (OC$_3$H$_6$O) and T is (pOOC$_6$H$_4$CO).

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening Agents

Fabric softening agents can also be incorporated into laundry detergent compositions in accordance with the present invention. These agents may be inorganic or organic in type. Inorganic softening agents are exemplified by the smectite clays disclosed in GB-A-1 400 898 and in U.S. Pat. No. 5,019,292. Organic fabric softening agents include the water insoluble tertiary amines as disclosed in GB-A-1 514 276 and EP 0 011 340 and their combination with mono C12-C14 quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric Dye-Transfer Inhibiting Agents

The detergent compositions according to the present invention may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinyl-pyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in liquid, paste, gels, bars or granular forms.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e., they may have a relatively higher density than conventional granular detergents, i.e., form 550 to 950 g/l; in such case, the granular detergent compositions according to the present invention will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, most preferably less than 10% by weight of the detergent compositions.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The following examples are meant to exemplify compositions for the present invention, but are not necessarily meant to limit or otherwise define the scope of the invention.

In the detergent compositions, the abbreviated component identifications have the following meanings:

LAS: Sodium linear C12 alkyl benzene sulphonate
TAS: Sodium tallow alkyl sulphate
XYAS: Sodium C1X-C1Y alkyl sulfate
SS: Secondary soap surfactant of formula 2-butyl octanoic acid
25EY: A C12-C15 predominantly linear primary alcohol condensed with an average of Y moles of ethylene oxide
45EY: A C14-C15 predominantly linear primary alcohol condensed with an average of Y moles of ethylene oxide
XYEZS: C1X-C1Y sodium alkyl sulfate condensed with an average of Z moles of ethylene oxide per mole
Nonionic: C13-C15 mixed ethoxylated/propoxylated fatty alcohol with an average degree of ethoxylation of 3.8 and an average degree of propoxylation of 4.5 sold under the tradename Plurafax LF404 by BASF Gmbh
CFAA: C12-C14 alkyl N-methyl glucamide
TFAA: C16-C18 alkyl N-methyl glucamide
Silicate: Amorphous Sodium Silicate ($SiO_2$:$Na_2O$ ratio=2.0)
NaSKS-6: Crystalline layered silicate of formula d-$Na_2Si_2O_5$
Carbonate: Anhydrous sodium carbonate
Phosphate: Sodium tripolyphosphate
MA/AA: Copolymer of 1:4 maleic/acrylic acid, average molecular weight about 80,000
Polyacrylate: Polyacrylate homopolymer with an average molecular weight of 8,000 sold under the tradename PA30 by BASF Gmbh
Zeolite A: Hydrated Sodium Aluminosilicate of formula $Na_{12}(AlO_2SiO_2)_{12} \cdot 27H_2O$ having a primary particle size in the range from 1 to 10 micrometers
Citrate: Tri-sodium citrate dihydrate
Citric: Citric Acid
Perborate: Anhydrous sodium perborate monohydrate bleach, empirical formula $NaBO_2 \cdot H_2O_2$
PB4: Anhydrous sodium perborate tetrahydrate
Percarbonate: Anhydrous sodium percarbonate bleach of empirical formula $2Na_2CO_3 \cdot 3H_2O_2$
TAED: Tetraacetyl ethylene diamine
CMC: Sodium carboxymethyl cellulose
DETPMP: Diethylene triamine penta(methylene phosphonic acid), marketed by Monsanto under the Tradename Dequest 2060
PVP: Polyvinylpyrrolidone polymer
EDDS: Ethylenediamine-N,N'-disuccinic acid, [S,S] isomer in the form of the sodium salt
Suds Suppressor: 25% paraffin wax Mpt 50° C., 17% hydrophobic silica, 58% paraffin oil
Granular Suds suppressor: 12% Silicone/silica, 18% stearyl alcohol, 70% starch in granular form
Sulphate: Anhydrous sodium sulphate
HMWPEO: High molecular weight polyethylene oxide
TAE 25: Tallow alcohol ethoxylate (25)

Detergent Example I

A granular fabric cleaning composition in accordance with the invention may be prepared as follows:

| | |
|---|---|
| Sodium linear C12 alkyl benzene sulfonate | 6.5 |

-continued

| | |
|---|---|
| Sodium sulfate | 15.0 |
| Zeolite A | 26.0 |
| Sodium nitrilotriacetate | 5.0 |
| Enzyme of the invention | 0.1 |
| PVP | 0.5 |
| TAED | 3.0 |
| Boric acid | 4.0 |
| Perborate | 18.0 |
| Phenol sulphonate | 0.1 |
| Minors | Up to 100 |

Detergent Example II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme of the invention | 0.1 |
| TAED | 6.0 |
| Percarbonate | 22.0 |
| EDDS | 0.3 |
| Granular suds suppressor | 3.5 |
| water/minors | Up to 100% |

Detergent Example III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme of the invention | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinylimidazole and vinylpyrrolidone | — | 0.2 |
| Perborate | 1.0 | — |
| Phenol sulfonate | 0.2 | — |
| Water/Minors | Up to 100% | |

Detergent Example IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

Heavy duty liquid fabric cleaning compositions in accordance with the invention may be prepared as follows:

| | I | II |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme of the invention | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

Textile Applications

In another embodiment, the present invention relates to use of the endoglucanase of the invention in the bio-polishing process. Bio-Polishing is a specific treatment of the yarn surface which improves fabric quality with respect to handle and appearance without loss of fabric wettability. The most important effects of Bio-Polishing can be characterized by less fuzz and pilling, increased gloss/luster, improved fabric handle, increased durable softness and altered water absorbency. Bio-Polishing usually takes place in the wet processing of the manufacture of knitted and woven fabrics. Wet processing comprises such steps as, e.g., desizing, scouring, bleaching, washing, dying/printing and finishing. During each of these steps, the fabric is more or less subjected to mechanical action. In general, after the textiles have been knitted or woven, the fabric proceeds to a desizing stage, followed by a scouring stage, etc. Desizing is the act of removing size from textiles. Prior to weaving on mechanical looms, warp yarns are often coated with size starch or starch derivatives in order to increase their tensile strength. After weaving, the size coating must be removed before further processing the fabric in order to ensure a homogeneous and wash-proof result. It is known that in order to achieve the effects of Bio-Polishing, a combination of cellulytic and mechanical action is required. It is also known that "super-softness" is achievable when the treatment with a cellulase is combined with a conventional treatment with softening agents. It is contemplated that use of the endoglucanase of the invention for bio-polishing of cellulosic fabrics is advantageous, e.g., a more thorough polishing can be achieved. Bio-polishing may be obtained by applying the method described, e.g., in WO 93/20278.

Stone-Washing

It is known to provide a "stone-washed" look (localized abrasion of the color) in dyed fabric, especially in denim fabric or jeans, either by washing the denim or jeans made from such fabric in the presence of pumice stones to provide the desired localized lightening of the color of the fabric or by treating the fabric enzymatically, in particular with cellulytic enzymes. The treatment with an endoglucanase of the present invention may be carried out either alone such as disclosed in U.S. Pat. No. 4,832,864, together with a smaller amount of pumice than required in the traditional process, or together with perlite such as disclosed in WO 95/09225.

Pulp and Paper Applications

In the papermaking pulp industry, the endoglucanase of the present invention may be applied advantageously, e.g., as follows:

For debarking: pretreatment with the endoglucanase may degrade the cambium layer prior to debarking in mechanical drums resulting in advantageous energy savings.

For defibration: treatment of a material containing cellulosic fibers with the endoglucanase prior to refining or beating may result in reduction of the energy consumption due to the hydrolyzing effect of the cellulase on the interfiber surfaces. Use of the endoglucanase may result in improved energy savings as compared to the use of known enzymes, since it is believed that the enzyme composition of the invention may possess a higher ability to penetrate fiber walls.

For fiber modification, i.e., improvement of fiber properties where partial hydrolysis across the fiber wall is needed which requires deeper penetrating enzymes (e.g., in order to make coarse fibers more flexible). Deep treatment of fibers has so far not been possible for high yield pulps, e.g., mechanical pulps or mixtures of recycled pulps. This has been ascribed to the nature of the fiber wall structure that prevents the passage of enzyme molecules due to physical restriction of the pore matrix of the fiber wall. It is contemplated that the present endoglucanase is capable of penetrating into the fiber wall.

For drainage improvement. The drainability of papermaking pulps may be improved by treatment of the pulp with hydrolysing enzymes, e.g., cellulases. Use of the present endoglucanase may be more effective, e.g., result in a higher degree of loosening bundles of strongly hydrated micro-fibrils in the fines fraction (consisting of fiber debris) that limits the rate of drainage by blocking hollow spaces between fibers and in the wire mesh of the paper machine. The Canadian standard freeness (CSF) increases and the Schopper-Riegler drainage index decreases when pulp in subjected to cellulase treatment, see, e.g., U.S. Pat. No. 4,923,565; TAPPI T227, SCAN C19:65.ence.

For inter fiber bonding. Hydrolytic enzymes are applied in the manufacture of papermaking pulps for improving the inter fiber bonding. The enzymes rinse the fiber surfaces for impurities, e.g., cellulosic debris, thus enhancing the area of exposed cellulose with attachment to the fiber wall, thus improving the fiber-to-fiber hydrogen binding capacity. This process is also referred to as dehornification. Paper and board produced with a cellulase containing enzyme preparation may have an improved strength or a reduced grammage, a smoother surface and an improved printability.

For enzymatic deinking. Partial hydrolysis of recycled paper during or upon pulping by use of hydrolysing enzymes such as cellulases are known to facilitate the removal and agglomeration of ink particles. Use of the present endoglucanase may give a more effective loosening of ink from the surface structure due to a better penetration of the enzyme molecules into the fibrillar matrix of the fiber wall, thus softening the surface whereby ink particles are effectively loosened. The agglomeration of loosened ink particles are also improved, due to a more efficient hydrolysis of cellulosic fragments found attached to ink particles originating from the fibers.

The treatment of lignocellulosic pulp may, e.g., be performed as described in WO 91/14819, WO 91/14822, WO 92/17573 and WO 92/18688.

Degradation of Plant Material

In yet another embodiment, the present invention relates to use of the endoglucanase and/or enzyme preparation according to the invention for degradation of plant material, e.g., cell walls.

It is contemplated that the novel endoglucanase and/or enzyme preparation of the invention is useful in the preparation of wine, fruit or vegetable juice in order to increase yield. Endoglucanases according to the invention may also be applied for enzymatic hydrolysis of various plant cell-wall derived materials or waste materials, e.g., agricultural residues such as wheat-straw, corn cobs, whole corn plants, nut shells, grass, vegetable hulls, bean hulls, spent grains, sugar beet pulp, and the like. The plant material may be degraded in order to improve different kinds of processing, facilitate purification or extraction of other components like purification of beta-glucan or beta-glucan oligomers from cereals, improve the feed value, decrease the water binding capacity, improve the degradability in waste water plants, improve the conversion of, e.g., grass and corn to ensilage, etc.

Examples

The invention is further illustrated in the following examples which are not intended to be in any way limiting to the scope of the invention as claimed.

Materials and Methods

Cellulolytic Activity

The cellulase variants of the invention show improved performance. Some of the variants may show improved performance with respect to increased catalytic activity.

In the context of this invention, cellulase activity can be expressed in S-CEVU. Cellulolytic enzymes hydrolyse CMC, thereby increasing the viscosity of the incubation mixture. The resulting reduction in viscosity may be determined by a vibration viscosimeter (e.g., MIVI 3000 from Sofraser, France).

Determination of the cellulolytic activity, measured in terms of S-CEVU, may be determined according to the following analysis method (assay): The S-CEVU assay quantifies the amount of catalytic activity present in the sample by measuring the ability of the sample to reduce the viscosity of a solution of carboxy-methylcellulose (CMC). The assay is carried out at 40° C.; pH 7.5; 0.1 M phosphate buffer; time 30 min; using a relative enzyme standard for reducing the viscosity of the CMC (carboxymethylcellulose Hercules 7 LFD) substrate; enzyme concentration approx. 0.15 S-CEVU/ml. The arch standard is defined to 8200 S-CEVU/g.

Example 1

Preparation of Cellulase Variants

Based on the disclosed sequence alignment (Table 1) and computer modeling method, position 119 was identified as a particular point of interest for making cellulase variants. Position 119 (cellulase numbering) is located within 3 Å from the substrate. In position 119 the wild-type *Humicola insolens* cellulase holds a histidine residue (H), whereas the wild-type *Thielavia terrestris* cellulase holds a glutamine residue (Q).

In this experiment, histidine was substituted for glutamine in the *Thielavia terrestris* cellulase (thereby obtaining the cellulase variant *Thielavia terrestris*/Q119H). The variant obtained was tested for specific activity.

All *Humicola insolens* variants are, unless otherwise stated, constructed by application of the Chameleon™ Double-stranded, site-directed Mutagenesis kit, from Stratagene. The following synthetic oligo-nucleotides were used as selection primers:

```
                                        (SEQ ID NO: 12)
    S/M  GAATGACTTGGTTGACGCGTCACCAGTCAC,
    or
                                        (SEQ ID NO: 13)
    M/S  GAATGACTTGGTTGAGTACTCACCAGTCAC.
```

S/M replaces the ScaI site in the beta-lactamase gene of the plasmid with a MluI site and M/S does the reverse. The latter is used to introduce secondary mutations in variants generated by the first selection primer.

For construction of *Thielavia terrestris* cellulase variants, the *Thielavia terrestris* EG V cellulase cDNA obtainable from the plasmid deposited as DSM 10811 was used. DSM 10811 was deposited at the Deutsche Sammlung von Mikroorganismen und Zellkulturen on 30 Jun. 1995 according to the Budapest Treaty. The plasmid was digested with the restriction endonucleases BamHI and NotI The 4153 bp vector part and the 1211 bp BamHI-NotI fragment were isolated. Equal portions of the 1211 bp fragment were digested with respectively HgiAI and EcoRV and the 487 bp BamHI-HgiAI and 690 bp EcoRV-NotI fragments were isolated.

These fragments and the vector part were ligated in the presence of 5 fold molar excess of a synthetic DNA fragment, resulting from the annealing of two single stranded DNA oligomers:

```
                                        (SEQ ID NO: 14)
    18802:  CACTGGCGGCGACCTGGGATCTAACCACTTCGAT (SEQ ID NO: 15)
    18803:  ATCGAAGTGGTTAGATCCCAGGTCGCCGCCTGTGCTC
```

The ligation mixture was transformed into *E. coli* strain XL1, and from the resulting transformants *Thielavia terrestris*/Q119H was isolated and verified by DNA sequencing.

All the cellulase variants ware produced by cloning the gene and transforming the gene into *Aspergillus oryzae* using a plasmid with the gene inserted between the fungal amylase promoter and the AMG terminator from *A. niger* [Christensen, T. Wöldike, H. Boel, E., Mortensen, S. B., Hjortshøj, K., Thim, L. and Hansen, M. T. (1988) Biotechnology 6: 1419-1422].

The cellulases with a cellulose binding domain CBD were purified by exploiting their binding to Avicel. The cloned product was recovered after fermentation by separation of the extracellular fluid from the production organism. The cellulase was then highly purified by affinity chromatography using 150 gram of Avicel in a slurry with 20 mM sodium-phosphate pH 7.5. The Avicel slurry was mixed with the crude fermentation broth which in total contains about 1 gram of protein. After mixing at 4° C. for 20 min, the Avicel-bound enzyme is packed into a column with a dimension of 50 times 200 mm about 400 ml total.

The column is washed with the 200 ml buffer, then washed with 0.5 M NaCl in the same buffer until no more protein elutes, and washed with 500 ml buffer (20 mM Tris pH 8.5). Finally the pure full length enzyme is eluted with 1% Triethylamine pH 11.8. The eluted enzyme solution is adjusted to pH 8 and concentrated using an Amicon cell unit with a membrane DOW GR61PP (polypropylene with a cut off of 20 KD) to 5 mg protein per ml. The enzymes have all been purified yielding a single band on SDS-PAGE.

Cellulases which natural lack CBD or the linker has been proteolytic cleaved or in which the CBD has been removed by introducing a stop codon after the catalytic domain, can not be purified using Avicel. The extracellular proteins are recovered free from the production organism. The core cellulases were purified free of *Aspergillus* proteins by cation exchange chromatography. The fermentation broth was adjusted to pH 3.5 and filtered to remove the precipitating proteins. Then the proteins were ultra filtrated (concentrated and washed with water) on a DOW GR81PP membrane with a cut off 6 KD until the conductivity of the eluate is below 1000 mS/cm. The sample was finally applied to an S-Sepharose column equilibrated with a 20 mM citrate buffer pH 3.5.

The enzyme will bind to the S-Sepharose at this low pH and it is eluted as a single peak using a NaCl gradient from 0 to 500 mM. The eluted pure enzyme was concentrated on a Amicon cell with the DOW GR81PP membrane. All purified cellulases gave a single band in SDS-PAGE.

The specific activity data are summarized in the following table:

| Enzyme/variant | Specific activity [%] |
|---|---|
| *Humicola insolens* | 100 |
| *Thielavia terrestris* | 35 |
| *Thielavia terrestris*/Q119H | 92 |

From this experiment it is seen that by introducing the mutation Q119H into the *Thielavia terrestris* cellulase, the specific activity if the resulting cellulase variants was increased to the level of that of the homologous *Humicola insolens* cellulase.

Example 2

Thielavia terrestris Variant with Improved Alkaline Performance Profile

In this experiment the *Thielavia terrestris*/Q119D was constructed as described in example 1 but using the following construction: For easy cassette swap and standard primer utilization, the CT1 encoding DNA was furnished with a C-terminal Xba1 site and subcloned into the pCaHj418 vector as described below. PCT1 was used as template in a Pwo polymerase PCR, 94° C., 2'-3×(94° C., 30"-72° C., 1')-25× (94° C., 30"-55° C., 30"-72° C., 1')-72° C., 5' applying the two primers

```
8939:   CGACTTCAATGTCCAGTCGG            (SEQ ID NO: 16)
25335:  GCGCTCTAGAGGATTAAAGGCACTGC      (SEQ ID NO: 17)
```

The resulting 718 bp PCR product was digested with Sal1 and Xba1 and the 165 bp fragment was isolated. This fragment was ligated together with the 833 bp BamH1-Sal1 fragment from pCT1-2 into the 4.1 kb Xba1-BamH1 vector fragment of pCaHj418.

From this ligation pCT1418 was isolated from *E. coli* transformants.

PCT2 was constructed by the Chameleon™ Double-stranded, site-directed Mutagenesis kit (from Stratagene) as described above with pCT1418 as template, the S/M primer as selection primer and the following mutagenic primer:

```
                                         (SEQ ID NO: 18)
109330: CGACCTGGGATCGAACGACTTCGATATCGCCATGC
```

A successfully mutated plasmid pCT2 was isolated, verified by DNA sequencing and transformed into *Aspergillus oryzae* strain JaL228.

The *Thielavia terrestris* cellulase and the *Thielavia terrestris*/Q119D variant was tested for activity towards PASC as described in example 9 at pH 7.0 and pH 10.0.

The results are presented in the table below which shows the activity at pH10 compared to the activity at pH 7. This demonstrates that the *Thielavia terrestris*/Q119D variant has relatively more alkaline activity as compared to the parent *Thielavia terrestris*.

|  | Relative activity pH 10/pH 7 [%] |
| --- | --- |
| *Thielavia terrestris* | 27 |
| *Thielavia terrestris*/Q119D | 62 |

Example 3

Construction of a Cellulase Hybrid Variant

The plasmid pCT3 embodies DNA encoding the *Thielavia terrestris* endoglucanase core enzyme and followed by the linker CBD of *Humicola grisea*.

pCT3 was constructed by means of sequence overlap extension PCR, applying PWO polymerase.

From a cDNA clone of *Humicola grisea* a 415 bp fragment was generated by the following primers:

```
                                      (SEQ ID NO: 19)
109452: CGACTCCAGCTTCCCCGTCTTCACGCCCCC (SEQ ID NO: 20)
107819: CGAGCTTCTAGATCTCGACTAGAGGCACTGGGAG
```

From pCT1418 (disclosed in example 2) an 876 bp PCR fragment was generated by the following primers:

```
                                      (SEQ ID NO: 21)
101621: GGATGCCATGCTTGGAGGATAGCAACC (SEQ ID NO: 22)
107823: GGGGGCGTGAAGACGGGAAGCTGGAGTCG
```

For both reactions the following set up was used: 96° C., 1'-3×(94° C., 30"-50° C., 1'-72° C., 1')-25×(94° C., 30"-61° C., 30"-72° C., 1')-72° C., 7'.

The isolated PCR fragments were applied as template in an assembly PCR reaction with primers 101621 and 107819: 94° C., 1'-3×(94° C., 30"-70° C., 1'-72° C., 2')-20×(94° C., 30"-61° C., 30"-72° C., 1.5')-72° C., 7'. The resulting 1261 bp PCR product was isolated cut by restriction enzymes BamH1 and Xba1 and the resulting 1172 bp DNA fragment was isolated and ligated into the 4.1 kb vector fragment of BamH1-Xba1 digested pCaHj418.

Correct clones were isolated and verified by DNA sequencing of plasmids isolated from *E. coli* XL1 transformants resulting above ligation reaction.

cDNA sequence of *Humicola grisea* (SEQ ID NO: 23):
CAAGAACCTCACACTCATTTTATTCACGCTCATTTATTCTAAAACTTCAA

TATGCGCTCTGCTCCTATTTTCCGCACGGCCCTGGCGGCTGCGCTCCCCC

TTGCCGCACTCGCCGCCGATGGCAAGTCGACCAGATACTGGGACTGCTGC

AAGCCATCGTGCTCTTGGCCCGGAAAGGCACTCGTGAACCAGCCTGTCTT

CACTTGCGACGCCAAATTCCAGCGCATCACCGACCCCAATACCAAGTCGG

GCTGCGATGGCGGCTCGGCCTTTTCGTGTGCTGACCAGACCCCCTGGGCT

CTGAACGACGATGTCGCCTATGGCTTCGCTGCCACGGCTATTTCGGGTGG

ATCGGAAGCCTCGTGGTGCTGCGCATGCTACGCTCTTACTTTCACCTCGG

GCCCTGTGGCCGGCAAGACCATGGTCGTCCAGTCGACCAACACCGGCGGC

GATCTCGGCAGCAACCATTTCGACCTCCAGATTCCAGGCGGCGGTGTCGG

CATCTTTGATGGGTGCACCCCCCAGTTCGGAGGTCTCGCTGGCGAACGCT

ACGGTGGCATCTCAGACCGCAGCTCCTGCGACTCGTTCCCTGCGGCGCTC

AAGCCCGGCTGCCTCTGGCGCTTCGATTGGTTCAAGAACGCCGACAACCC

GACCTTTACCTTCAAGCAGGTGCAGTGCCCCGCCGAGCTTGTTGCCAGGA

CCGGCTGCAAGCGCGAGGATGACGGCAACTTCCCCGTCTTCACGCCCCCC

GCGGGTAGCAACACCGGCGGTAGCCAGTCGAGCTCCACTATCGCTTCCAG

CTCGACCTCCAAGGCTCAGACTTCGGCCGCCAGCTCCACCTCCAAGGCTG

TCGTGACTCCCGTCTCCAGCTCCACCTCGAAGGCCGCTGAGGTCCCCAAA

TCCAGCTCGACCTCCAAGGCTGCCGAGGTCGCCAAGCCCAGCTCAACTTC

GACCTCGACCTCGACCTCGACCAAGGTCAGCTGCTCTGCGACCGGTGGCT

-continued
CCTGCGTCGCTCAGAAGTGGGCGCAGTGCGGCGGCAATGGCTTCACCGGC

TGCACGTCGTGCGTCAGCGGCACCACCTGCCAGAAGCAAAATGACTGGTA

CTCCCAGTGCCTCTAAGTCGTTTGTAGTAGCAGTTTGAAGGATGTCAGGG

ATGAGGGAGGGAGGAGTGGGGGAAAAGTACGCCGCAGTTTTTTGGTAGAC

TTACTGTATTGTTGAGTAATTACCCATTCGCTTCTTGTACGAAAAAAAAA

AAAAAAAAAAA

Example 4

Construction of Variants of a Hybrid Cellulase

The plasmid pPsF45 embodies DNA encoding the *Pseudomonas cellolytica* endoglucanase core enzyme headed by the *H. insolens* EGV endoglucanase signal peptide and followed by the linker CBD of same enzyme.

Two variants of this hybrid enzyme were constructed by means of the above-mentioned Stratagene Chameleon® kit: PsF45/H15S and PsF45/Q119H (cellulase numbering) by application of the following mutagenic primers

```
PsF45/H15S:
                                (SEQ ID NO: 24)
GCTGCAAGCCGTCCTGTGGCTGGAGCGCTAACGTGCCCGCG

PsF45/Q119H:
                                (SEQ ID NO: 25)
CGATGTTTCCGGAGGCCACTTTGACATTCTGGTTCC
```

Deviations from template sequence are indicated in bold type.

The selection primer was converting the unique Sca1 site in the lactamase gene of the plasmid to a Mlu1 site:

```
GAATGACTTGGTTGACGCGTCACCAGTCAC    (SEQ ID NO: 26)
```

The two variants were verified by DNA sequencing and one correct version of each variant was identified.

The two plasmids enharboring the variant sequences pPsF45H15S and pPsF45Q119H were used to transform *A. oryzae* strain JaL142 together with the AMDS selection plasmid pToC202. From the resulting transformants LaC2829 and LaC 2830 were isolated after 3 reisolation steps via spores.

Example 5

Removal of Disulfide Bridges

Disulfide bridges are known to stabilize protein structures. The removal of disulfide bridges in a cellulase will destabilizes the enzyme (thermostability) while retaining significant activity. This can be useful in applications where a fast inactivation of the enzyme is preferred, e.g., in denim or textile applications or for low temperature processes.

In this example *Humicola insolens* EGV cellulase and five variants of *Humicola insolens* cellulase were constructed mutating either one or both residues involved in a disulfide bridge. The specific activity was measured as disclosed under Materials and Methods. The melting temperature of the enzymes was measured using Differential Scanning Calorimetry, DSC. DSC was done at neutral pH (7.0) using a Micro-Calc Inc. MC calorimeter with a constant scan rate and raising the temperature from 20° C. to 90° C. at a rate of 90° C. per hour.

The results are presented in the table below which shows that removal of a disulfide bridge leads to a variant with a significantly lower melting temperature but retaining significant activity.

|  | Specific activity [%] | Melting temp. [° C.] |
|---|---|---|
| *Humicola insolens* | 100 | 81 |
| *Humicola insolens*/C12G, C47M | 15 | 63.7 |
| *Humicola insolens*/C12M, C47G | 53 | 64.3 |
| *Humicola insolens*/C47G | 48 | 57.3 |
| *Humicola insolens*/C87M, C199G | 75 | 63.4 |
| *Humicola insolens*/C16M, C86G | 103 | 59.2 |

Example 6

Mutation of Conserved Residues in the Binding Cleft <5 Å from Substrate

When comparing the positions within a distance of 5 Å from the substrate to the sequence alignment in Table 1 the type of amino acid residue at these positions are conserved in the aligned cellulases for the following positions: 6, 7, 8, 9, 10, 11, 12, 18, 45, 112, 114, 121, 127, 128, 130, 132, 147, 148, and 149. Conserved residues are normally thought to be extremely important for the activity, but the inventors have found that a certain variability is allowed while maintaining significant activity. Only the two residues D10 and D121 (cellulase numbering) are necessary to maintain reasonable activity.

Variants of the *Humicola insolens* EGV cellulase were prepared and the specific activity was measured as disclosed in Materials and Methods.

The type of mutations and the variants specific activity are summarized in the following table:

| Variant | Specific activity [%] |
|---|---|
| *Humicola insolens* | 100 |
| *Humicola insolens*/T6S | 34 |
| *Humicola insolens*/R7I | 33 |
| *Humicola insolens*/R7W | 29 |
| *Humicola insolens*/Y8F | 67 |
| *Humicola insolens*/W9F | 83 |
| *Humicola insolens*/C12M, C47G | 53 |
| *Humicola insolens*/W18Y | 49 |
| *Humicola insolens*/W18F | 53 |
| *Humicola insolens*/S45T | 85 |
| *Humicola insolens*/S45N | 85 |
| *Humicola insolens*/D114N | 6 |
| *Humicola insolens*/F132D | 11 |
| *Humicola insolens*/Y147D | 34 |
| *Humicola insolens*/Y147C | 30 |
| *Humicola insolens*/Y147W | 74 |
| *Humicola insolens*/Y147V | 33 |
| *Humicola insolens*/Y147R | 45 |
| *Humicola insolens*/Y147G | 34 |
| *Humicola insolens*/Y147Q | 41 |
| *Humicola insolens*/Y147N | 53 |
| *Humicola insolens*/Y147K | 45 |
| *Humicola insolens*/Y147H | 75 |
| *Humicola insolens*/Y147F | 57 |
| *Humicola insolens*/Y147S | 55 |

From this experiment it is seen that mutating conserved residues in the binding cleft can be performed while retaining significant activity of the cellulase variant.

Example 7

Mutation of Non-Conserved Residues in the Binding Cleft <5 Å from the Substrate Based on the sequence alignment in Table 1 and the disclosed computer modeling method the following residues located within a distance of 5 Å from the substrate and not being conserved amongst the aligned sequences in were identified as points of interest for making cellulase variants.

In this experiment non-conserved residues located no more than 5 Å from the substrate were modified in the *Humicola insolens* EGV cellulase and the specific activity was measured as described under Materials and Methods.

The type of mutations and the variants specific activity are summarized in the following table:

|  | Specific activity [%] |
|---|---|
| *Humicola insolens* | 100 |
| *Humicola insolens*/R4H | 73 |
| *Humicola insolens*/R4Q | 70 |
| *Humicola insolens*/K13L | 37 |
| *Humicola insolens*/K13R | 100 |
| *Humicola insolens*/K13Q | 38 |
| *Humicola insolens*/P14A | 99 |
| *Humicola insolens*/P14T | 71 |
| *Humicola insolens*/S15T | 18 |
| *Humicola insolens*/S15H | 10 |
| *Humicola insolens*/C16M, C86G | 103 |
| *Humicola insolens*/A19P | 51 |
| *Humicola insolens*/A19T | 84 |
| *Humicola insolens*/A19G | 78 |
| *Humicola insolens*/A19S | 89 |
| *Humicola insolens*/K20G | 91 |
| *Humicola insolens*/D42Y | 102 |
| *Humicola insolens*/D42W | 103 |
| *Humicola insolens*/C47G | 48 |
| *Humicola insolens*/E48D | 93 |
| *Humicola insolens*/E48Q | 71 |
| *Humicola insolens*/E48D, P49* | 88 |
| *Humicola insolens*/E48N, P49* | 79 |
| *Humicola insolens*/S110N | 94 |
| *Humicola insolens*/L115I | 18 |
| *Humicola insolens*/G116D | 71 |
| *Humicola insolens*/H119R | 15 |
| *Humicola insolens*/H119Q | 39 |
| *Humicola insolens*/H119F | 11 |
| *Humicola insolens*/N123A | 61 |
| *Humicola insolens*/N123M | 80 |
| *Humicola insolens*/N123Q | 76 |
| *Humicola insolens*/N123Y | 8 |
| *Humicola insolens*/N123D | 86 |
| *Humicola insolens*/V129L | 72 |
| *Humicola insolens*/D133N | 102 |
| *Humicola insolens*/D178N | 81 |

From this experiment it is seen that most of the non-conserved residues in the binding cleft can be mutated while retaining all or most of the activity of the cellulase.

Example 8

Resistance to Anionic Surfactants in Detergent

A. Variants of the present invention may show improved performance with respect to an altered sensitivity towards anionic tensides. Anionic tensides are products frequently incorporated into detergent compositions. Unfolding of cellulases tested so far, is accompanied by a decay in the intrinsic fluorescence of the proteins. The intrinsic fluorescence derives from Trp side chains (and to a smaller extent Tyr side chains) and is sensitive to the hydrophobicity of the side chain environment. Unfolding leads to a more hydrophilic environment as the side-chains become more exposed to solvent, and this quenches fluorescence.

Fluorescence is followed on a Perkin/Elmer™ LS50 luminescence spectrometer. In practice, the greatest change in fluorescence on unfolding is obtained by excitation at 280 nm and emission at 345 nm. Slit widths (which regulate the magnitude of the signal) are usually 5 nm for both emission and excitation at a protein concentration of 5 micrograms/ml. Fluorescence is measured in 2-ml quartz cuvettes thermostatted with a circulating water bath and stirred with a small magnet. The magnet-stirrer is built into the spectrometer.

Unfolding can be followed in real time using the available software. Rapid unfolding (going to completion within less than 5-10 minutes) is monitored in the TimeDrive option, in which the fluorescence is measured every few (2-5) seconds. For slower unfolding, four cuvettes can be measured at a time in the cuvette-holder using the Wavelength Program option, in which the fluorescence of each cuvette is measured every 30 seconds. In all cases, unfolding is initiated by adding a small volume (typically 50 microliters) of concentrated enzyme solution to the thermostatted cuvette solution where mixing is complete within a few seconds due to the rapid rotation of the magnet.

Data are measured in the software program GraphPad Prism. Unfolding fits in all cases to a single-exponential function from which a single half-time of unfolding (or unfolding rate constant) can be obtained.

Typical unfolding conditions are:
a. 10 mM CAPS pH 10, 1000 ppm LAS, 40° C.
b. 10 mM HEPES pH 10, 200 ppm LAS, 25° C.

In both cases, the protein concentration is 5-10 micrograms/ml (the protein concentration is not crucial, as LAS is in excess). Under these conditions, the unfolding of *Humicola insolens* cellulase can be compared with other enzymes (Table 1). This enables us to draw up the following ranking order for stability against anionic tenside:

*Thielavia terrestris*/Q119H≅*Thielavia terrestris*>>*Humicola insolens*≅*Humicola insolens*/H119Q.

| Cellulase | t½ pH 10 (s) (1000 ppm LAS, 40° C.) | t½ pH 7 (s) (200 ppm LAS, 25° C.) |
|---|---|---|
| *Humicola insolens* | 48 | 28 |
| *Humicola insolens*/H119Q | 63 | 9a |
| *Thielavia terrestris* | 970 | 690 |
| *Thielavia terrestris*/Q119H | 1100 | 550 | aUnfolding is double-exponential. The t½ of the slower phase is approx. 120 sec.

B. The alteration of the surface electrostatics of an enzyme will influence the sensibility towards anionic tensides such as LAS (linear alkylbenzenesulfonate). Especially variants where positive charged residues have been removed and/or negatively charged residues have been introduced will increase the resistance towards LAS, whereas the opposite, i.e., the introduction of positively charged residues and/or the removal of negatively charged residues will lower the resistance towards LAS. The residues Arg (R), Lys (K) and His (H) are viewed as positively or potentially positively charged residue and the residues Asp (D), Glu (E) and Cys (C) if not included in a disulphide bridge are viewed as negatively or potentially negatively charged residues. Positions already containing one of these residues are the primary target for mutagenesis, secondary targets are positions which have one of these residues on an equivalent position in another cellulase, and third target are any surface exposed residue. In this experiment wild type *Humicola insolens* cellulase are being compared to *Humicola insolens* cellulase variants belonging to all three of the above groups, comparing the stability towards LAS in detergent.

Cellulase resistance to anionic surfactants was measured as activity on PASC (phosphoric acid swollen cellulose) in the presence of anionic surfactant vs. activity on PASC in the absence of anionic surfactant.

The reaction medium contained 5.0 g/l of a commercial regular powder detergent from the detergent manufacturer NOPA Denmark. The detergent was formulated without surfactants for this experiment and pH adjusted to pH 7.0. Further the reaction medium included 0.5 g/l PASC and was with or without 1 g/l LAS (linear alkylbenzenesulphonate), which is an anionic surfactant, and the reaction proceeded at the temperature 30° C. for 30 minutes. Cellulase was dosed at 0.20 S-CEVU/I. After the 30 minutes of incubation the reaction was stopped with 2 N NaOH and the amount of reducing sugar ends determined through reduction of p-hydroxybenzoic acid hydrazide. The decrease in absorption of reduced p-hydroxybenzoic acid hydrazide relates to the cellulase activity.

The type of mutation and the resistance towards LAS for variants with increased LAS resistance is summarized in the following table:

| Variant | Relative LAS resistance [%] |
| --- | --- |
| *Humicola insolens* | 100 |
| *Humicola insolens*/R158E | 341 |
| *Humicola insolens*/Y8F, W62E, A162P, | 179 |
| *Humicola insolens*/R158E, A162P | 347 |
| *Humicola insolens*/R158G | 322 |
| *Humicola insolens*/S152D | 161 |
| *Humicola insolens*/R158E/R196E | 319 |
| *Humicola insolens*/R158E, D161P, A162P | 351 |
| *Humicola insolens*/R4H, R158E, D161P, A162P | 344 |
| *Humicola insolens*/H119Q | 148 |
| *Humicola insolens*/Y8F, W62E, R252L, Y280F | 131 |
| *Humicola insolens*/R252L, Y280F | 133 |
| *Humicola insolens*/W62E, A162P | 130 |
| *Humicola insolens*/W62E, A162P | 129 |
| *Humicola insolens*/S117D | 143 |
| *Humicola insolens*/A57C, A162C | 134 |
| *Humicola insolens*/N154D | 149 |
| *Humicola insolens*/R4H, D161P, A162P, R196E | 134 |

From this table it is seen that mutations of residues resulting in the removal of positively charged residue and/or the introduction of a negatively charged residue increase the resistance towards LAS.

As described above the type of mutation and the resistance towards LAS for variants with decreased LAS resistance is summarized in the following table:

| Variant | Relative LAS resistance [%] |
| --- | --- |
| *Humicola insolens* | 100 |
| *Humicola insolens*/Y147H | 71 |
| *Humicola insolens*/E192P | 52 |
| *Humicola insolens*/D161P, A162P | 64 |
| *Humicola insolens*/D67T | 44 |
| *Humicola insolens*/Q36T, D67T | 67 |
| *Humicola insolens*/D66N | 47 |
| *Humicola insolens*/D67N | 71 |
| *Humicola insolens*/V64R | 58 |
| *Humicola insolens*/N65R | 48 |
| *Humicola insolens*/T93R | 60 |
| *Humicola insolens*/Q36T, D67T, A83T | 64 |
| *Humicola insolens*/E91Q | 71 |
| *Humicola insolens*/A191K | 63 |
| *Humicola insolens*/D42W | 67 |
| *Humicola insolens*/S117K | 62 |
| *Humicola insolens*/R4H, A63R, N65R, D67R | 54 |
| *Humicola insolens*/D133N | 0 |
| *Humicola insolens*/D58A | 15 |
| *Humicola insolens*/D67R | 39 |
| *Humicola insolens*/A63R | 38 |
| *Humicola insolens*/R37N, D58A | 6 |
| *Humicola insolens*/K175R | 32 |
| *Humicola insolens*/D2N | 43 |
| *Humicola insolens*/N65R, D67R | 40 |
| *Humicola insolens*/T136D, G141R | 5 |
| *Humicola insolens*/Y147K | 17 |
| *Humicola insolens*/Y147R | 1 |
| *Humicola insolens*/D161P | 35 |
| *Humicola insolens*/D66P | 40 |
| *Humicola insolens*/D66A, D67T | 39 |
| *Humicola insolens*/D67T, *143NGT | 7 |
| *Humicola insolens*/Q36T, D67T, *143NGT | 0 |
| *Humicola insolens*/N65R, D67R, S76K | 22 |
| *Humicola insolens*/W62R | 25 |
| *Humicola insolens*/S117R, F120S | 31 |
| *Humicola insolens*/K13R | 16 |
| *Humicola insolens*/D10E | 0 |

From this table it is seen that mutations of residues resulting in the introduction of positively charged residue and/or the removal of a negatively charged residue decrease the resistance towards LAS.

Example 9

Alteration of pH Activity Profile

The pH activity profile of a cellulase is governed by the pH dependent behavior of specific titratable groups, typically the acidic residues in the active site. The pH profile can be altered by changing the electrostatic environment of these residues, either by substitution of residues involving charged or potentially charged groups such as Arg (R), Lys (K), Tyr (Y), His (H), Glu (E), Asp (D) or Cys (C) if not involved in a disulphide bridge or by changes in the surface accessibility of these specific titratable groups by mutations in the biding cleft within 5 Å of the substrate.

In this example *Humicola insolens* cellulase and variants of *Humicola insolens* cellulase involving substitution of charged or potentially charged residues have been tested for activity towards PASC at pH 7 and pH 10, respectively.

In order to determine the pH optimum for cellulases we have selected organic buffers because it is common known that, e.g., borate forms covalent complexes with mono- and oligo-saccharides and phosphate can precipitate with Ca-ions. In DATA FOR BIOCHEMICAL RESEARCH Third Edition OXFORD SCIENCE PUBLICATIONS page 223 to 241, suitable organic buffers have been found. In respect of their pKa values we decided to use Na-acetate in the range 4-5.5, MES at 6.0, MOPS in the range 6.5-7.5, Na-barbiturate 8.0-8.5 and glycine in the range 9.0-10.5.

Method:
The method is enzymatic degradation of carboxy-methyl-cellulose, at different pH's. Buffers are prepared in the range 4.0 to 10.5 with intervals of 0.5 pH unit. The analysis is based on formation of new reducing ends in carboxy-methyl-cellulose, these are visualized by reaction with PHBAH in strong alkaline environment, were they forms a yellow compound with absorption maximum at 410 nm.

Experimental Protocol:

Buffer preparation: 0.2 mol of each buffer substance is weighed out and dissolved in 1 liter of Milli Q water. 250 ml 0.2 M buffer solution and 200 ml Milli Q water is mixed. The pH is measured using Radiometer PHM92 labmeter calibrated using standard buffer solutions from Radiometer. The pH of the buffers are adjusted to actual pH using 4 M NaOH or 4 M HCl and adjusted to total 500 ml with water. When adjusting Na-barbiturate to pH 8.0 there might be some precipitation, this can be re-dissolved by heating to 50° C.

Acetic acid 100% 0.2 mol=12.01 g.
MES 0.2 mol=39.04 g.
MOPS 0.2 mol=41.86 g.
Na-barbiturate 0.2 mol=41.24 g.
Glycine 0.2 mol=15.01 g.

Buffers:
pH: 4.0, 4.5, 5.0 & 5.5 Na-acetate 0.1 M
pH: 6.0 Na-MES 0.1 M
pH: 6.5, 7.0 & 7.5 Na-MOPS 0.1 M
pH: 8.0 & 8.5 Na-barbiturate 0.1 M
pH: 9.0, 9.5, 10.0 & 10.5 Na.glycine 0.1 M The actual pH is measured in a series treated as the main values, but without stop reagent, pH is measured after 20 min. incubation at 40° C.

Substrate Preparation:

2.0 g CMC, in 250 ml conic glass flask with a magnet rod, is moistened with 2.5 ml. 96% ethanol, 100 ml. Milli Q water is added and then boiled to transparency on a heating magnetic stirrer. Approximately 2 min. boiling. Cooled to room temperature on magnetic stirrer.

Stop Reagent:
1.5 g PHBAH and 5 g K—Na-tartrate dissolved in 2% NaOH.

Procedure:
There are made 3 main values and 2 blank value using 5 ml glass test tubes. (1 main value for pH determination)

|  | Main values | Blank value |
|---|---|---|
| Buffer | 1.0 ml. | 1.0 ml. |
| Substrate CMC | 0.75 ml. | 0.75 ml. |
| Mix | 5 sec. | 5 sec. |
| Preheat | 10 min./40° C. | — |
| Enzyme | 0.25 ml. | — |
| Mix | 5 sec. | — |
| Incubation | 20 min./40° C. | room temp. |
| PHBAH-reagent | 1 ml. | 1 ml. |
| Mix | 5 sec. | — |
| Enzyme | — | 0.25 ml. |
| Mix | — | 5 sec. |

Mixing on a Heidolph REAX 2000 mixer with permanent mix and maximum speed (9). No stirring during incubation on water bath with temperature control. Immediately after adding PHBAH-reagent and mixing the samples are boiled 10 min. Cooled in cold tap water for 5 min. Absorbance read at 410 nm.

Determination of Activity

The absorbance at 410 nm from the 2 Main values are added and divided by 2 and the 2 Blank values are added and divided by 2, the 2 mean values are subtracted. The percentages are calculated by using the highest value as 100%.

The measured pH is plotted against the relative activity.

Buffer Reagents:
Acetic acid 100% from MERCK cat. no. 1.00063, batch no. K20928263 422, pKa 4.76, MW 60.05;
MES (2[N-Morpholino]ethanesulfonic acid) from SIGMA cat. no. M-8250, batch no. 68F-5625, pKa 6.09, MW 195.2;
MOPS (3-[N-Morpholino]propanesulfonic acid) from SIGMA cat. no. M-1254, batch no. 115F-5629, pKa 7.15, MW 209.3;
Na-barbiturate (5,5-Diethylbarbituric acid sodium salt) from MERCK cat. no. 6318, batch no. K20238018 404, pKa 7.98, MW 206.2;
Glycine from MERCK cat. no. 4201, batch no. K205535601 405, pKa 9.78, MW 75.07;
PHBAH (p-hydroxy benzoic acid hydrazide) from SIGMA cat. no. H-9882, batch no. 53H7704;
K—Na-tartrate (Potassium sodium tartrate tetrahydrate) from MERCK cat. no. 8087, batch no. A653387 304;
NaOH (Sodium hydroxide) from MERCK cat. no. 1.06498, batch no. C294798 404;
CMC (Carboxy Methyl Cellulose) supplied by Hercules (FMC)7LF (November 1989).

Cellulase resistance to anionic surfactants was measured as activity on PASC (phosphoric acid swollen cellulose) at neutral pH (pH 7.0) vs. activity on PASC at alkaline pH (pH 10.0).

The reaction medium contained 5.0 g/l of a commercial regular powder detergent from the detergent manufacturer NOPA Denmark. The pH was adjusted to pH 7.0 and pH 10.0, respectively. Further the reaction medium included 0.5 g/l PASC, and the reaction proceeded at the temperature 30° C. for 30 minutes. Cellulase was dosed at 0.20 S-CEVU/l. After the 30 minutes of incubation the reaction was stopped with 2 N NaOH and the amount of reducing sugar ends determined through reduction of p-hydroxybenzoic acid hydrazide. The decrease in absorption of reduced p-hydroxybenzoic acid hydrazide relates to the cellulase activity.

Results:
The results are presented in the table below, the activity at pH 10 relative to pH 7 is compared to that of wild type *Humicola insolens* cellulase.

| Variant | PASC activity pH 10/pH 7 relative to wild type [%] |
|---|---|
| *Humicola insolens* | 100 |
| *Humicola insolens*/S76K, S117D | 120 |
| *Humicola insolens*/V129L | 133 |
| *Humicola insolens*/R4H, A63R, N65R, D67R | 120 |
| *Humicola insolens*/R252L, Y280F | 115 |
| *Humicola insolens*/D161P, A162P | 117 |
| *Humicola insolens*/A57C, A162C | 110 |
| *Humicola insolens*/S76K | 117 |
| *Humicola insolens*/D161P, A162P, R196E | 113 |
| *Humicola insolens*/Q36T, D67T, A83T | 111 |
| *Humicola insolens*/W62R | 112 |
| *Humicola insolens*/D42Y | 110 |
| *Humicola insolens*/S76K, A78K | 114 |
| *Humicola insolens*/S76K, A78R | 118 |

From the above table it is seen that the relative alkaline activity can be increased by creating variants involving potentially charged residues and/or by altering residues in the binding cleft less that 5 Å from the substrate.

Similarly the following table shows that the relative acidic activity can be increased by other mutations involving potentially charged residues and/or by altering residues in the binding cleft less than 5 Å from the substrate.

| Variant | PASC activity pH 10/pH 7 relative to wild type [%] |
|---|---|
| Humicola insolens | 100 |
| Humicola insolens/D58A | 83 |
| Humicola insolens/Y280W | 90 |
| Humicola insolens/D67R | 89 |
| Humicola insolens/A63R | 85 |
| Humicola insolens/Y8F | 82 |
| Humicola insolens/W62E | 82 |
| Humicola insolens/R37N, D58A | 84 |
| Humicola insolens/K175G | 81 |
| Humicola insolens/K175R | 82 |
| Humicola insolens/Y8F, M104Q | 83 |
| Humicola insolens/Y8F, W62E, R252L, Y280F | 83 |
| Humicola insolens/W62E, A162P | 87 |
| Humicola insolens/Y8F, W62E, A162P | 88 |
| Humicola insolens/Y147H | 90 |
| Humicola insolens/Y147N | 90 |
| Humicola insolens/Y147Q | 85 |
| Humicola insolens/Y147W | 85 |
| Humicola insolens/E192P | 89 |
| Humicola insolens/R158G | 83 |
| Humicola insolens/S152D | 90 |
| Humicola insolens/K13Q | 82 |
| Humicola insolens/R37P | 82 |
| Humicola insolens/S45T | 87 |
| Humicola insolens/E48D | 86 |
| Humicola insolens/R7I | 83 |
| Humicola insolens/P14A | 84 |
| Humicola insolens/A19G | 90 |
| Humicola insolens/A19T | 90 |
| Humicola insolens/R4H, D161P, A162P, R196E | 88 |
| Humicola insolens/D133N | 80 |
| Humicola insolens/D40N | 40 |
| Humicola insolens/Y90F | 72 |
| Humicola insolens/A63D | 78 |
| Humicola insolens/G127S, I131A, A162P, Y280F, R252L | 25 |
| Humicola insolens/Y147S | 39 |
| Humicola insolens/Y147F | 71 |
| Humicola insolens/T6S | 44 |
| Humicola insolens/S55E | 14 |
| Humicola insolens/N123D | 35 |
| Humicola insolens/N123Y | 71 |
| Humicola insolens/R158E | 78 |
| Humicola insolens/T136D, G141R | 57 |
| Humicola insolens/G127S, I131A, A162P | 52 |
| Humicola insolens/W62E, G127S, I131A, A162P, Y280F, R252L | 35 |
| Humicola insolens/W62E, G127S, I131A, A162P | 58 |
| Humicola insolens/W62E, G127S, I131A | 64 |
| Humicola insolens/W62E, G127S, I131A, Y280F, R252L | 80 |
| Humicola insolens/H119Q | 57 |
| Humicola insolens/Y8F, W62E | 61 |
| Humicola insolens/W62E, A162P | 76 |
| Humicola insolens/W62E, A162P | 80 |
| Humicola insolens/R158E, A162P | 80 |
| Humicola insolens/Y8F, Y147S | 63 |
| Humicola insolens/Y147R | 54 |
| Humicola insolens/Y147V | 22 |
| Humicola insolens/Y147C | 67 |
| Humicola insolens/Y147D | 60 |
| Humicola insolens/N154D | 74 |
| Humicola insolens/R158E, R196E | 79 |
| Humicola insolens/R158E, D161P, A162P | 70 |
| Humicola insolens/D67T, *143NGT | 65 |
| Humicola insolens/Q36T, D67T, *143NGT | 53 |
| Humicola insolens/143*NGW, Q145D | 53 |
| Humicola insolens/L142P, 143*NGW, Q145E | 42 |
| Humicola insolens/N65R, D67R, S76K | 60 |
| Humicola insolens/A63R, N65R, D67R | 77 |
| Humicola insolens/T93R | 80 |
| Humicola insolens/S76R | 70 |
| Humicola insolens/S117R, F120S | 58 |
| Humicola insolens/N123Q | 63 |
| Humicola insolens/N123M | 49 |
| Humicola insolens/N123A | 80 |
| Humicola insolens/E48D, P49* | 66 |
| Humicola insolens/S55Y | 61 |
| Humicola insolens/S55M | 48 |
| Humicola insolens/W18F | 54 |
| Humicola insolens/S45N | 71 |
| Humicola insolens/R7W | 58 |
| Humicola insolens/K13R | 72 |
| Humicola insolens/R7L | 74 |
| Humicola insolens/S15T | 38 |
| Humicola insolens/W18Y | 37 |
| Humicola insolens/C16M, C86G | 67 |
| Humicola insolens/K13L | 59 |
| Humicola insolens/C12M, C47G | 12 |
| Humicola insolens/W9F | 62 |
| Humicola insolens/C47G | 58 |
| Humicola insolens/C12G, C47M | 0 |
| Humicola insolens/D10E | 0 |
| Humicola insolens/R7K | 49 |

Accordingly, this example demonstrates that the relative activity pH profile can be altered towards acidic or alkaline pH by creation of variants involving potentially charged residues and/or by altering residues in the binding cleft less that 5 Å from the substrate.

Example 10

Wash Performance of Cellulases Made Resistant to Anionic Surfactants

Application effect of a cellulase made resistant to anionic surfactants vs. application effect of the native cellulase was measured as 'color clarification' of worn black cotton swatches laundered with cellulase in a 0.1 liter mini-Terg-o-Meter. Laundering was done in varying concentrations of anionic surfactant.

The reaction medium contained phosphate buffer pH 7.0 and varying concentrations of LAS in the range 0.2-1.0 g/L. Two swatches were laundered at 40° C. for 30 minutes, rinsed and then dried. This laundering cycle was repeated four times. All enzymes were tested at each LAS concentration.

Finally the black cotton swatches were graded against a standard of similar swatches washed with varying dosages of the native cellulase, the fungal ~43 kD endo-beta-1,4-glucanase from *Humicola insolens*, DSM 1800, (commercially available under the tradename Carezyme®), and the effect expressed in PSU (panel score units).

| | LAS concentration | | | | |
|---|---|---|---|---|---|
| Variant | 0.2 g/l | 0.4 g/l | 0.6 g/l | 0.8 g/l | 1.0 g/l |
| Humicola insolens | 15 | 0 | 0 | 0 | 0 |
| Humicola insolens/ R158E | 30 | 14 | 30 | 22 | 11 |
| Humicola insolens/ R158G | 20 | 18 | 20 | 33 | 28 |

What is claimed is:

1. An isolated variant of a parent cellulase, consisting of 1-6 mutations wherein
   (a) the parent cellulase comprises the amino acid sequence of SEQ ID NO: 5;
   (b) one of the mutations is a substitution at position 119;
   (c) the variant has endoglucanase activity; and
   (d) the positions are numbered according to the amino acid sequence of the cellulase SEQ ID NO: 1.

2. The modified cellulase of claim 1, wherein the substitution at position 119 is with H or D.

3. The modified cellulase of claim 1, which consists of 1 mutation.

4. The modified cellulase of claim 1, which consists of 2 mutations.

5. The modified cellulase of claim 1, which consists of 3 mutations.

6. The modified cellulase of claim 1, which consists of 4 mutations.

7. The modified cellulase of claim 1, which consists of 5 mutations.

8. The modified cellulase of claim 1, which consists of 6 mutations.

9. A detergent composition comprising the variant of claim 1 and a surfactant.

* * * * *

SEQUENCE LISTING

<160> NUMBER OF SEQ ID NOS: 26

<210> SEQ ID NO 1
<211> LENGTH: 202
<212> TYPE: PRT
<213> ORGANISM: Humicola insolens

<400> SEQUENCE: 1

Ala Asp Gly Arg Ser Thr Arg Tyr Trp Asp Cys Cys Lys Pro Ser Cys
1               5                   10                  15

Gly Trp Ala Lys Lys Ala Pro Val Asn Gln Pro Val Phe Ser Cys Asn
            20                  25                  30

Ala Asn Phe Gln Arg Ile Thr Asp Phe Asp Ala Lys Ser Gly Cys Glu
        35                  40                  45

Pro Gly Gly Val Ala Tyr Ser Cys Ala Asp Gln Thr Pro Trp Ala Val
    50                  55                  60

Asn Asp Asp Phe Ala Leu Gly Phe Ala Ala Thr Ser Ile Ala Gly Ser
65                  70                  75                  80

Asn Glu Ala Gly Trp Cys Cys Ala Cys Tyr Glu Leu Thr Phe Thr Ser
                85                  90                  95

Gly Pro Val Ala Gly Lys Lys Met Val Val Gln Ser Thr Ser Thr Gly
            100                 105                 110

Gly Asp Leu Gly Ser Asn His Phe Asp Leu Asn Ile Pro Gly Gly Gly
        115                 120                 125

Val Gly Ile Phe Asp Gly Cys Thr Pro Gln Phe Gly Gly Leu Pro Gly
    130                 135                 140

Gln Arg Tyr Gly Gly Ile Ser Ser Arg Asn Glu Cys Asp Arg Phe Pro
145                 150                 155                 160

Asp Ala Leu Lys Pro Gly Cys Tyr Trp Arg Phe Asp Trp Phe Lys Asn
                165                 170                 175

Ala Asp Asn Pro Ser Phe Ser Phe Arg Gln Val Gln Cys Pro Ala Glu
            180                 185                 190

Leu Val Ala Arg Thr Gly Cys Arg Arg Ala
        195                 200

<210> SEQ ID NO 2
<211> LENGTH: 202
<212> TYPE: PRT
<213> ORGANISM: Acremonium sp.

<400> SEQUENCE: 2

Gly Ser Gly His Thr Thr Arg Tyr Trp Asp Cys Cys Lys Pro Ser Cys
1               5                   10                  15

Ala Trp Asp Glu Lys Ala Ala Val Ser Arg Pro Val Thr Thr Cys Asp
            20                  25                  30

Arg Asn Asn Ser Pro Leu Ser Pro Gly Ala Val Ser Gly Cys Asp Pro
        35                  40                  45

Asn Gly Val Ala Phe Thr Cys Asn Asp Asn Gln Pro Trp Ala Val Asn
    50                  55                  60

Asn Asn Val Ala Tyr Gly Phe Ala Ala Thr Ala Phe Pro Gly Gly Asn
65                  70                  75                  80

Glu Ala Ser Trp Cys Cys Ala Cys Tyr Ala Leu Gln Phe Thr Ser Gly
                85                  90                  95

Pro Val Ala Gly Lys Thr Met Val Val Gln Ser Thr Asn Thr Gly Gly
            100                 105                 110

```
Asp Leu Ser Gly Thr His Phe Asp Ile Gln Met Pro Gly Gly Leu
            115                 120                 125

Gly Ile Phe Asp Gly Cys Thr Pro Gln Phe Gly Phe Thr Phe Pro Gly
        130                 135                 140

Asn Arg Tyr Gly Gly Thr Thr Ser Arg Ser Gln Cys Ala Glu Leu Pro
145                 150                 155                 160

Ser Val Leu Arg Asp Gly Cys His Trp Arg Tyr Asp Trp Phe Asn Asp
                165                 170                 175

Ala Asp Asn Pro Asn Val Asn Trp Arg Arg Val Arg Cys Pro Ala Ala
            180                 185                 190

Leu Thr Asn Arg Ser Gly Cys Val Arg Ala
            195                 200
```

<210> SEQ ID NO 3
<211> LENGTH: 202
<212> TYPE: PRT
<213> ORGANISM: Volutella collectotrichoides

<400> SEQUENCE: 3

```
Gly Thr Gly Arg Thr Thr Arg Tyr Trp Asp Cys Cys Lys Pro

```
                    35                  40                  45
Gly Gly Ser Ala Tyr Thr Cys Ala Asn Asn Ser Pro Trp Ala Val Asn
 50                  55                  60

Asp Asn Leu Ala Tyr Gly Phe Ala Ala Thr Lys Leu Ser Gly Gly Thr
 65                  70                  75                  80

Glu Ser Ser Trp Cys Cys Ala Cys Tyr Ala Leu Thr Phe Thr Ser Gly
                 85                  90                  95

Pro Val Ser Gly Lys Thr Leu Val Val Gln Ser Thr Ser Thr Gly Gly
                100                 105                 110

Asp Leu Gly Ser Asn His Phe Asp Leu Asn Met Pro Gly Gly Gly Val
            115                 120                 125

Gly Leu Phe Asp Gly Cys Lys Arg Glu Phe Gly Gly Leu Pro Gly Ala
        130                 135                 140

Gln Tyr Gly Gly Ile Ser Ser Arg Ser Glu Cys Asp Ser Phe Pro Ala
145                 150                 155                 160

Ala Leu Lys Pro Gly Cys Gln Trp Arg Phe Asp Trp Phe Lys Asn Ala
                165                 170                 175

Asp Asn Pro Glu Phe Thr Phe Lys Gln Val Gln Cys Pro Ser Glu Leu
            180                 185                 190

Thr Ser Arg Thr Gly Cys Lys Arg Ala
        195                 200

<210> SEQ ID NO 5
<211> LENGTH: 201
<212> TYPE: PRT
<213> ORGANISM: Thielavia terrestris

<400> SEQUENCE: 5

Gly Ser Gly Gln Ser Thr Arg Tyr Trp Asp Cys Cys Lys Pro Ser Cys
 1               5                  10                  15

Ala Trp Pro Gly Lys Ala Ala Val Ser Gln Pro Val Tyr Ala Cys Asp
                20                  25                  30

Ala Asn Phe Gln Arg Leu Ser Asp Phe Asn Val Gln Ser Gly Cys Asn
            35                  40                  45

Gly Gly Ser Ala Tyr Ser Cys Ala Asp Gln Thr Pro Trp Ala Val Asn
 50                  55                  60

Asp Asn Leu Ala Tyr Gly Phe Ala Ala Thr Ser Ile Ala Gly Gly Ser
 65                  70                  75                  80

Glu Ser Ser Trp Cys Cys Ala Cys Tyr Ala Leu Thr Phe Thr Ser Gly
                 85                  90                  95

Pro Val Ala Gly Lys Thr Met Val Val Gln Ser Thr Ser Thr Gly Gly
                100                 105                 110

Asp Leu Gly Ser Asn Gln Phe Asp Ile Ala Met Pro Gly Gly Gly Val
            115                 120                 125

Gly Ile Phe Asn Gly Cys Ser Ser Gln Phe Gly Gly Leu Pro Gly Ala
        130                 135                 140

Gln Tyr Gly Gly Ile Ser Ser Arg Asp Gln Cys Asp Ser Phe Pro Ala
145                 150                 155                 160

Pro Leu Lys Pro Gly Cys Gln Trp Arg Phe Asp Trp Phe Gln Asn Ala
                165                 170                 175

Asp Asn Pro Thr Phe Thr Phe Gln Gln Val Gln Cys Pro Ala Glu Ile
            180                 185                 190

Val Ala Arg Ser Gly Cys Lys Arg Ala
        195                 200
```

<210> SEQ ID NO 6
<211> LENGTH: 203
<212> TYPE: PRT
<213> ORGANISM: Fusarium oxysporum

<400> SEQUENCE: 6

Gly Ser Gly His Ser Thr Arg Tyr Trp Asp Cys Cys Lys Pro Ser Cys
1               5                   10                  15

Ser Trp Ser Gly Lys Ala Ala Val Asn Ala Pro Ala Leu Thr Cys Asp
            20                  25                  30

Lys Asn Asp Asn Pro Ile Ser Asn Thr Asn Ala Val Asn Gly Cys Glu
        35                  40                  45

Gly Gly Gly Ser Ala Tyr Ala Cys Thr Asn Tyr Ser Pro Trp Ala Val
    50                  55                  60

Asn Asp Glu Leu Ala Tyr Gly Phe Ala Ala Thr Lys Ile Ser Gly Gly
65                  70                  75                  80

Ser Glu Ala Ser Trp Cys Cys Ala Cys Tyr Ala Leu Thr Phe Thr Thr
                85                  90                  95

Gly Pro Val Lys Gly Lys Lys Met Ile Val Gln Ser Thr Asn Thr Gly
            100                 105                 110

Gly Asp Leu Gly Asp Asn His Phe Asp Leu Met Met Pro Gly Gly Gly
        115                 120                 125

Val Gly Ile Phe Asp Gly Cys Thr Ser Glu Phe Gly Lys Ala Leu Gly
    130                 135                 140

Gly Ala Gln Tyr Gly Gly Ile Ser Ser Arg Ser Glu Cys Asp Ser Tyr
145                 150                 155                 160

Pro Glu Leu Leu Lys Asp Gly Cys His Trp Arg Phe Asp Trp Phe Glu
                165                 170                 175

Asn Ala Asp Asn Pro Asp Phe Thr Phe Glu Gln Val Gln Cys Pro Lys
            180                 185                 190

Ala Leu Leu Asp Ile Ser Gly Cys Lys Arg Ala
        195                 200

<210> SEQ ID NO 7
<211> LENGTH: 205
<212> TYPE: PRT
<213> ORGANISM: Myceliophthora thermophila

<400> SEQUENCE: 7

Gly Ile Gly Gln Thr Thr Arg Tyr Trp Asp Cys Cys Lys Pro Ser Cys
1               5                   10                  15

Ala Trp Pro Gly Lys Gly Pro Ser Ser Pro Val Gln Ala Cys Asp Lys
            20                  25                  30

Asn Asp Asn Pro Phe Asn Asp Gly Gly Ser Thr Arg Ser Gly Cys Asp
        35                  40                  45

Ala Gly Gly Ser Ala Tyr Met Cys Ser Ser Gln Ser Pro Trp Ala Val
    50                  55                  60

Ser Asp Glu Leu Ser Tyr Gly Trp Ala Ala Val Lys Leu Ala Gly Ser
65                  70                  75                  80

Ser Glu Ser Gln Trp Cys Cys Ala Cys Tyr Glu Leu Thr Phe Thr Ser
                85                  90                  95

Gly Pro Val Ala Gly Lys Lys Met Ile Val Gln Ala Thr Asn Thr Gly
            100                 105                 110

Gly Asp Leu Gly Asp Asn His Phe Asp Leu Ala Ile Pro Gly Gly Gly
        115                 120                 125

Val Gly Ile Phe Asn Ala Cys Thr Asp Gln Tyr Gly Ala Pro Pro Asn
    130                 135                 140

Gly Trp Gly Asp Arg Tyr Gly Ile His Ser Lys Glu Glu Cys Glu
145                 150                 155                 160

Ser Phe Pro Glu Ala Leu Lys Pro Gly Cys Asn Trp Arg Phe Asp Trp
            165                 170                 175

Phe Gln Asn Ala Asp Asn Pro Ser Val Thr Phe Gln Glu Val Ala Cys
        180                 185                 190

Pro Ser Glu Leu Thr Ser Lys Ser Gly Cys Ser Arg Ala
        195                 200                 205

<210> SEQ ID NO 8
<211> LENGTH: 203
<212> TYPE: PRT
<213> ORGANISM: Crinipellis scabella

<400> SEQUENCE: 8

Thr Ala Gly Val Thr Thr Arg Tyr Trp Asp Cys Cys Lys Pro Ser Cys
1               5                   10                  15

Gly Trp Ser Gly Lys Ala Ser Val Ser Ala Pro Val Arg Thr Cys Asp
            20                  25                  30

Arg Asn Gly Asn Thr Leu Gly Pro Asp Val Lys Ser Gly Cys Asp Ser
        35                  40                  45

Gly Gly Thr Ser Phe Thr Cys Ala Asn Asn Gly Pro Phe Ala Ile Asp
    50                  55                  60

Asn Asn Thr Ala Tyr Gly Phe Ala Ala His Leu Ala Gly Ser Ser
65              70                  75                  80

Glu Ala Ala Trp Cys Cys Gln Cys Tyr Glu Leu Thr Phe Thr Ser Gly
                85                  90                  95

Pro Val Val Gly Lys Lys Leu Thr Val Gln Val Thr Asn Thr Gly Gly
            100                 105                 110

Asp Leu Gly Asn Asn His Phe Asp Leu Met Ile Pro Gly Gly Gly Val
        115                 120                 125

Gly Leu Phe Thr Gln Gly Cys Pro Ala Gln Phe Gly Ser Trp Asn Gly
    130                 135                 140

Gly Ala Gln Tyr Gly Gly Val Ser Ser Arg Asp Gln Cys Ser Gln Leu
145                 150                 155                 160

Pro Ala Ala Val Gln Ala Gly Cys Gln Phe Arg Phe Asp Trp Met Gly
            165                 170                 175

Gly Ala Asp Asn Pro Asn Val Thr Phe Arg Pro Val Thr Cys Pro Ala
        180                 185                 190

Gln Leu Thr Asn Ile Ser Gly Cys Val Arg Ala
        195                 200

<210> SEQ ID NO 9
<211> LENGTH: 203
<212> TYPE: PRT
<213> ORGANISM: Macrophomina phaseolina

<400> SEQUENCE: 9

Thr Ser Gly Val Thr Thr Arg Tyr Trp Asp Cys Cys Lys Pro Ser Cys
1               5                   10                  15

Ala Trp Thr Gly Lys Ala Ser Val Ser Lys Pro Val Gly Thr Cys Asp
            20                  25                  30

Ile Asn Asp Asn Ala Gln Thr Pro Ser Asp Leu Leu Lys Ser Ser Cys
        35                  40                  45

Asp Gly Gly Ser Ala Tyr Tyr Cys Ser Asn Gln Gly Pro Trp Ala Val
    50                  55                  60

Asn Asp Ser Leu Ser Tyr Gly Phe Ala Ala Lys Leu Ser Gly Lys
 65                  70                  75                  80

Gln Glu Thr Asp Trp Cys Cys Gly Cys Tyr Lys Leu Thr Phe Thr Ser
                 85                  90                  95

Thr Ala Val Ser Gly Lys Gln Met Ile Val Gln Ile Thr Asn Thr Gly
                100                 105                 110

Gly Asp Leu Gly Asn Asn His Phe Asp Ile Ala Met Pro Gly Gly Gly
                115                 120                 125

Val Gly Ile Phe Asn Gly Cys Ser Lys Gln Trp Asn Gly Ile Asn Leu
            130                 135                 140

Gly Asn Gln Tyr Gly Gly Phe Thr Asp Arg Ser Gln Cys Ala Thr Leu
145                 150                 155                 160

Pro Ser Lys Trp Gln Ala Ser Cys Asn Trp Arg Phe Asp Trp Phe Glu
                165                 170                 175

Asn Ala Asp Asn Pro Thr Val Asp Trp Glu Pro Val Thr Cys Pro Gln
                180                 185                 190

Glu Leu Val Ala Arg Thr Gly Cys Ser Arg Ala
            195                 200

<210> SEQ ID NO 10
<211> LENGTH: 235
<212> TYPE: PRT
<213> ORGANISM: Pseudomonas fluorescens

<400> SEQUENCE: 10

Cys Asn Gly Tyr Ala Thr Arg Tyr Trp Asp Cys Cys Lys Pro His Cys
  1               5                  10                  15

Gly Trp Ser Ala Asn Val Pro Ser Leu Val Ser Pro Leu Gln Ser Cys
                 20                  25                  30

Ser Ala Asn Asn Thr Arg Leu Ser Asp Val Ser Val Gly Ser Ser Cys
                 35                  40                  45

Asp Gly Gly Gly Gly Tyr Met Cys Trp Asp Lys Ile Pro Phe Ala Val
             50                  55                  60

Ser Pro Thr Leu Ala Tyr Gly Tyr Ala Ala Thr Ser Ser Gly Asp Val
 65                  70                  75                  80

Cys Gly Arg Cys Tyr Gln Leu Gln Phe Thr Gly Ser Ser Tyr Asn Ala
                 85                  90                  95

Pro Gly Asp Pro Gly Ser Ala Ala Leu Ala Gly Lys Thr Met Ile Val
                100                 105                 110

Gln Ala Thr Asn Ile Gly Tyr Asp Val Ser Gly Gln Phe Asp Ile
            115                 120                 125

Leu Val Pro Gly Gly Gly Val Gly Ala Phe Asn Ala Cys Ser Ala Gln
            130                 135                 140

Trp Gly Val Ser Asn Ala Glu Leu Gly Ala Gln Tyr Gly Gly Phe Leu
145                 150                 155                 160

Ala Ala Cys Lys Gln Gln Leu Gly Tyr Asn Ala Ser Leu Ser Gln Tyr
                165                 170                 175

Lys Ser Cys Val Leu Asn Arg Cys Asp Ser Val Phe Gly Ser Arg Gly
                180                 185                 190

Leu Thr Gln Leu Gln Gln Gly Cys Thr Trp Phe Ala Glu Trp Phe Glu
            195                 200                 205

Ala Ala Asp Asn Pro Ser Leu Lys Tyr Lys Glu Val Pro Cys Pro Ala
            210                 215                 220

Glu Leu Thr Thr Arg Ser Gly Met Asn Arg Ala
225                 230                 235

```
<210> SEQ ID NO 11
<211> LENGTH: 211
<212> TYPE: PRT
<213> ORGANISM: Ustilago maydis

<400> SEQUENCE: 11

Gly Met Ala Thr Arg Tyr Trp Asp Cys Cys Leu Ala Ser Ala Ser Trp
1               5                   10                  15

Glu Gly Lys Ala Pro Val Tyr Ala Pro Val Asp Ala Cys Lys Ala Asp
            20                  25                  30

Gly Val Thr Leu Ile Asp Ser Lys Lys Asp Pro Ser Gly Gln Ser Gly
        35                  40                  45

Cys Asn Gly Gly Asn Lys Phe Met Cys Ser Cys Met Gln Pro Phe Asp
    50                  55                  60

Asp Glu Thr Asp Pro Thr Leu Ala Phe Gly Phe Gly Ala Phe Thr Thr
65                  70                  75                  80

Gly Gln Glu Ser Asp Thr Asp Cys Ala Cys Phe Tyr Ala Glu Phe Glu
                85                  90                  95

His Asp Ala Gln Gly Lys Ala Met Lys Arg Asn Lys Leu Ile Phe Gln
            100                 105                 110

Val Thr Asn Val Gly Gly Asp Val Gln Ser Gln Asn Phe Asp Phe Gln
        115                 120                 125

Ile Pro Gly Gly Gly Leu Gly Ala Phe Pro Lys Gly Cys Pro Ala Gln
    130                 135                 140

Trp Gly Val Glu Ala Ser Leu Trp Gly Asp Gln Tyr Gly Gly Val Lys
145                 150                 155                 160

Ser Ala Thr Glu Cys Ser Lys Leu Pro Lys Pro Leu Gln Glu Gly Cys
                165                 170                 175

Lys Trp Arg Phe Ser Glu Trp Gly Asp Asn Pro Val Leu Lys Gly Ser
            180                 185                 190

Pro Lys Arg Val Lys Cys Pro Lys Ser Leu Ile Asp Arg Ser Gly Cys
        195                 200                 205

Gln Arg Ala
    210

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
gaatgacttg gttgacgcgt caccagtcac                                        30

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
gaatgacttg gttgagtact caccagtcac                                        30

<210> SEQ ID NO 14
<211> LENGTH: 34
<212> TYPE: DNA
<213> ORGANISM: Artificial Sequence
<220> FEATURE:
```

```
<223> OTHER INFORMATION: Primer

<400> SEQUENCE: 14
cactggcggc gacctgggat ctaaccactt cgat                            34

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
atcgaagtgg ttagatccca ggtcgccgcc tgtgctc                         37

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
cgacttcaat gtccagtcgg                                            20

<210> SEQ ID NO 17
<211> LENGTH: 26
<212> TYPE: DNA
<213> ORGANISM: Artificial Sequence
<220> FEATURE:
<223> OTHER INFORMATION: Primer

<400> SEQUENCE: 17
gcgctctaga ggattaaagg cactgc                                     26

<210> SEQ ID NO 18
<211> LENGTH: 35
<212> TYPE: DNA
<213> ORGANISM: Artificial Sequence
<220> FEATURE:
<223> OTHER INFORMATION: Primer

<400> SEQUENCE: 18
cgacctggga tcgaacgact tcgatatcgc catgc                           35

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
cgactccagc ttccccgtct tcacgccccc                                 30

<210> SEQ ID NO 20
<211> LENGTH: 34
<212> TYPE: DNA
<213> ORGANISM: Artificial Sequence
<220> FEATURE:
<223> OTHER INFORMATION: Primer

<400> SEQUENCE: 20
cgagcttcta gatctcgact agaggcactg ggag                            34

<210> SEQ ID NO 21
```

```
<211> LENGTH: 27
<212> TYPE: DNA
<213> ORGANISM: Artificial Sequence
<220> FEATURE:
<223> OTHER INFORMATION: Primer

<400> SEQUENCE: 21
ggatgccatg cttggaggat agcaacc                                        27

<210> SEQ ID NO 22
<211> LENGTH: 29
<212> TYPE: DNA
<213> ORGANISM: Artificial Sequence
<220> FEATURE:
<223> OTHER INFORMATION: Primer

<400> SEQUENCE: 22
gggggcgtga agacgggaag ctggagtcg                                      29

<210> SEQ ID NO 23
<211> LENGTH: 1081
<212> TYPE: DNA
<213> ORGANISM: Humicola grisea

<400> SEQUENCE: 23
ctcgtgaacc agcctgtctt cacttgcgac gccaaattcc agcgcatcac cgaccccaat    60
accaagtcgg gctgcgatgg cggctcggcc ttttcgtgtg ctgaccagac ccctgggct    120
ctgaacgacg atgtcgccta tggcttcgct gccacggcta tttcgggtgg atcggaagcc   180
tcgtggtgct gcgcatgcta cgctcttact ttcacctcgg gccctgtggc cggcaagacc   240
atggtcgtcc agtcgaccaa caccggcggc gatctcggca gcaaccattt cgacctccag   300
attccaggcg gcggtgtcgg catctttgat gggtgcaccc cccagttcgg aggtctcgct   360
ggcgaacgct acgtggcat ctcagaccgc agctcctgcg actcgttccc tgcggcgctc   420
aagcccggct gcctctggcg cttcgattgg ttcaagaacg ccgacaaccc gacctttacc   480
ttcaagcagg tgcagtgccc cgccgagctt gttgccagga ccggctgcaa gcgcgaggat   540
gacggcaact tccccgtctt cacgccccc gcgggtagca cacggcgg tagccagtcg    600
agctccacta tcgcttccag ctcgacctcc aaggctcaga cttcggccgc cagctccacc   660
tccaaggctg tcgtgactcc cgtctccagc tccacctcga aggccgctga ggtccccaaa   720
tccagctcga cctccaaggc tgccgaggtc gccaagccca gctcaacttc gacctcgacc   780
tcgacctcga ccaaggtcag ctgctctgcg accggtggct cctgcgtcgc tcagaagtgg   840
gcgcagtgcg gcggcaatgg cttcaccggc tgcacgtcgt gcgtcagcgg caccacctgc   900
cagaagcaaa atgactggta ctcccagtgc ctctaagtcg tttgtagtag cagtttgaag   960
gatgtcaggg atgagggagg gaggagtggg ggaaaagtac gccgcagttt tttggtagac  1020
ttactgtatt gttgagtaat tacccattcg cttcttgtac gaaaaaaaaa aaaaaaaaa   1080
a                                                                 1081

<210> SEQ ID NO 24
<211> LENGTH: 41
<212> TYPE: DNA
<213> ORGANISM: Artificial Sequence
<220> FEATURE:
<223> OTHER INFORMATION: Primer

<400> SEQUENCE: 24
gctgcaagcc gtcctgtggc tggagcgcta acgtgcccgc g                        41
```

```
<210> SEQ ID NO 25
<211> LENGTH: 36
<212> TYPE: DNA
<213> ORGANISM: Artificial Sequence
<220> FEATURE:
<223> OTHER INFORMATION: Primer

<400> SEQUENCE: 25
cgatgtttcc ggaggccact ttgacattct ggttcc                              36

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
gaatgacttg gttgacgcgt caccagtcac                                     30
```